US010176301B2

(12) United States Patent
Hill et al.

(10) Patent No.: US 10,176,301 B2
(45) Date of Patent: Jan. 8, 2019

(54) SYSTEMS, METHODS, AND SOFTWARE FOR PROVIDING A PATIENT-REPORTED OUTCOME MEASURE OF DYSPHAGIA PATIENTS WITH EOSINOPHILIC ESOPHAGITIS

(71) Applicant: Meritage Pharma Inc., Lexington, MA (US)

(72) Inventors: Malcolm Hill, Solana Beach, CA (US); Robert Farber, San Diego, CA (US); Bonnie Hepburn, Escondido, CA (US); Linda Gieschen, San Diego, CA (US)

(73) Assignee: MERITAGE PHARMA, INC., Lexington, MA (US)

( * ) Notice: Subject to any disclaimer, the term of this patent is extended or adjusted under 35 U.S.C. 154(b) by 595 days.

(21) Appl. No.: 14/851,695

(22) Filed: Sep. 11, 2015

(65) Prior Publication Data

US 2016/0078186 A1  Mar. 17, 2016

Related U.S. Application Data

(60) Provisional application No. 62/049,170, filed on Sep. 11, 2014.

(51) Int. Cl.
*G06F 19/00* (2018.01)
*G16H 50/20* (2018.01)
(Continued)

(52) U.S. Cl.
CPC .......... *G06F 19/345* (2013.01); *G16H 10/20* (2018.01); *G16H 10/60* (2018.01); *G16H 50/20* (2018.01)

(58) Field of Classification Search
None
See application file for complete search history.

(56) References Cited

U.S. PATENT DOCUMENTS 8,380,531 B2  2/2013  Paty et al.
8,428,966 B2  4/2013  Green, III et al.
(Continued)

FOREIGN PATENT DOCUMENTS

WO  2009/049278 A1  4/2009

OTHER PUBLICATIONS

Dellon et al., Development and field testing of a novel patient-reported outcome measure of dysphagia in patients with eosinophilic esophagitis, Jul. 9, 2013, Alimentary Pharmacology and Therapeutics, vol. 38, pp. 634-642, doi:10.1111/apt.12413.*
(Continued)

*Primary Examiner* — Lena Najarian
*Assistant Examiner* — Devin C Hein
(74) *Attorney, Agent, or Firm* — Troutman Sanders LLP

(57) ABSTRACT

Provided herein are computer-based systems, software, and methods of using the same including a daily patient questionnaire, the questionnaire comprising: a question for determining whether the patient avoided solid food; a question for determining whether the patient had difficulty swallowing solid food; a question for determining what action the patient took to correct or relieve difficulty swallowing food; a question for determining the amount of pain the patient experienced while swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

3 Claims, 26 Drawing Sheets

(51) Int. Cl.
  *G16H 10/20* (2018.01)
  *G16H 10/60* (2018.01)

(56) References Cited

U.S. PATENT DOCUMENTS

| | | |
|---|---|---|
| 8,696,568 B2 | 4/2014 | Jedwab et al. |
| 2012/0046641 A1* | 2/2012 | Jedwab .................. A61B 5/00 604/503 |
| 2013/0066652 A1 | 3/2013 | Heywood et al. |
| 2013/0110551 A1 | 5/2013 | Bingol |

OTHER PUBLICATIONS

Schoepfer et al., Development and Validation of a Symptom-Based Activity Index for Adults With Eosinophilic Esophagitis, Aug. 28, 2014, Gastroenterology, vol. 47, pp. 1255-1266.*

Aitken et al., "Patient apps for improved healthcare: from novelty to mainstream." IMS Institute for Healthcare Informatics, URL: <http://www.imshealth.com/deployedfiles/imshealth/Global/Content/Corporate/IMS_Health_Institute/Reports/Patient_Apps/IIHI_Patient_Apps_Report.pdf> accessed Oct. 27, 2014; publication date: Oct. 2013.

Eng et al., "Mobile health applications for diabetes and endocrinology: promise and peril?" Pediatr Diabetes. Jun. 2013; 14(4): 10.1111/pedi.12034.

Klonoff DC, "The current status of mHealth for diabetes: will it be the next big thing?" J Diabetes Sci Technol.May 1, 2013;7(3):749-758.

Straumann A et al., "Budesonide is effective in adolescent and adult patients with active eosinophilic esophagitis." Gastroenterology. Nov. 2010; 139(5):1526-1537.

* cited by examiner

Fig. 12

1. Since you woke up this morning, did you eat solid food?

Yes $_{(0)}$

No $_{(\ )}$

2. Since you woke up this morning, has food gone down slowly or been stuck in your throat or chest?

Yes $_{(1)}$

No $_{(0)}$

3. For the most difficult time you had swallowing food today, did you have to do anything to make the food go down or take action to get relief?

No, it got better or cleared up on its own $_{(0)}$

Yes, I had to drink liquid to get relief $_{(1)}$

Yes, I had to cough and/or gag to get relief $_{(2)}$

Yes, I had to vomit to get relief $_{(3)}$

Yes, I had to seek medical attention to get relief $_{(4)}$

*Dysphagia days per week ÷ number of days reported

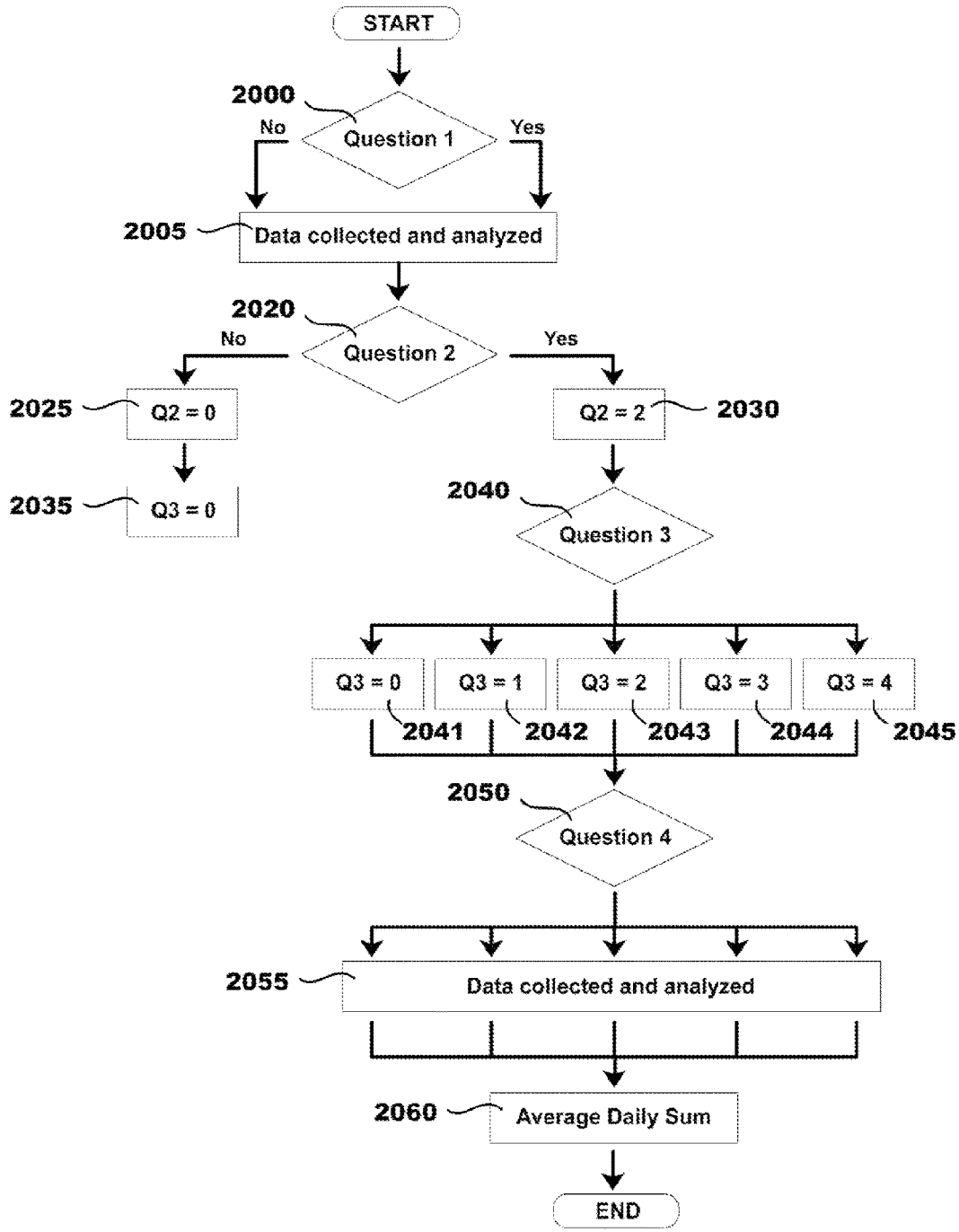

Fig. 21

Q1  Since you woke up this morning, did you eat solid food?

Possible responses = yes, no.

Q2  Since you woke up this morning, has food gone down slowly or been stuck in your throat?

Possible responses = yes (2), no (0).

Q3  For the most difficult time you had swallowing food today (during the past 24 hours), did you have to do anything to make the food go down or to get relief?

Possible responses:

No, it got better or cleared up on its own (0)

Yes, I had to drink liquid to get relief (1)

Yes, I had to cough and/or gag to get relief (2)

Yes, I had to vomit to get relief (3)

Yes, I had to seek medical attention to get relief (4)

Q4  The following question concerns the amount of pain you have experienced when swallowing food. What was the worst pain you had while swallowing food over the past 24 hours?

Possible responses:

None, I had no pain (0)

Mild (1)

Moderate (2)

Severe (3)

Very Severe (4)

SYSTEMS, METHODS, AND SOFTWARE FOR PROVIDING A PATIENT-REPORTED OUTCOME MEASURE OF DYSPHAGIA PATIENTS WITH EOSINOPHILIC ESOPHAGITIS

CROSS REFERENCE TO RELATED APPLICATION

The present application is a Non-Provisional application of U.S. Provisional Application Ser. No. 62/049,170, filed on Sep. 11, 2014. The contents of that application are incorporated herein by reference.

BACKGROUND OF THE INVENTION

Esophageal inflammation disorders are gaining increased recognition in both adults and children. One example is eosinophilic esophagitis (EoE), which is an emerging, and fast-growing disorder and can be characterized by high levels of eosinophils in the esophagus, and/or basal zone hyperplasia. Diagnosis of EoE is often made based on the finding of 15 to 20 or more to 24 or more eosinophils per high power field (eos/hpf) within esophageal mucosal biopsies taken at various heights in the esophagus.

In parallel with other atopic disorders, the incidence of EoE appears to be increasing. Symptoms of EoE include, for example, abdominal pain, chest pain, choking, difficulty swallowing, failure to thrive, nausea, reflux not relieved by standard anti-flux therapy, skin rash or hives, vomiting, and weight loss. In one series, 15% of EoE patients had concurrent developmental delay.

Although EoE is becoming more frequently diagnosed throughout the world many aspects of the disease remain unclear including its etiology, natural history and optimal therapy. For example, the overlap of gastroesophageal reflux disease (GERD) and EoE symptoms is common The common occurrence regarding misdiagnosis of EoE for GERD often results in delayed treatment for patients with EoE. One symptom that does not overlap is dysphagia. Elevated levels of eosinophils can lead to esophageal fibrosis resulting in loss of esophageal function potentially leading to dysphagia, or difficulty swallowing.

SUMMARY OF THE INVENTION

Previous instruments for assessing dysphagia rely on patients to recall their symptoms over an extended period of time and capture historic symptom information in oral or written form. Many previous instruments require administration by a third party. There is an unmet need for a tool to assess patient dysphagia symptoms in a convenient and self-administered format. Such a tool should be simple and only require a patient to recall their dysphagia symptoms experienced in the current 24-hour period.

Accordingly, in one aspect, the invention encompasses methods comprising the steps of: providing a daily patient questionnaire, said questionnaire comprising: a question for determining whether the patient avoided solid food; a question for determining whether the patient had difficulty swallowing solid food; contingent on an affirmative answer to said question for determining whether the patient had difficulty swallowing solid food, a question for determining what action the patient took to correct or relieve difficulty swallowing food; a question for determining the amount of pain the patient experienced while swallowing food; and applying an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia. In some embodiments, the patient has dysphagia associated with eosinophilic esophagitis. In some embodiments, the questionnaire is self-administered by said patient. In some embodiments, the patient is 12 to 45 years old. In some embodiments, the therapy comprises diet intervention therapy. In some embodiments, the therapy comprises pharmacologic therapy. In some embodiments, the therapy comprises immunotherapy. In further embodiments, the therapy comprises corticosteroid therapy. In still further embodiments, the therapy comprises oral administration of budesonide. In some embodiments, the therapy comprises mechanical dilation. In some embodiments, the algorithm incorporates symptom severity data. In some embodiments, the algorithm incorporates symptom frequency data. In some embodiments, the algorithm is optionally corrected for variations in patient compliance with completing a daily patient questionnaire. In some embodiments, the score is a daily average score. In further embodiments, the daily average score is determined over one week. In further embodiments, the daily average score is determined over more than one week. In some embodiments, the score illustrates one or more selected from the group consisting of: (1) severity, intensity, or frequency of patient dysphagia associated with eosinophilic esophagitis; (2) suitability of a patient for a particular diagnostic tool, diagnostic method, or therapy for dysphagia associated with eosinophilic esophagitis; and (3) efficacy of a particular therapy for dysphagia associated with eosinophilic esophagitis. In some embodiments, the score illustrates suitability of a patient for inclusion in a clinical trial. In some embodiments, the score illustrates a patient's compliance in a clinical trial. In some embodiments, the score illustrates reduction in esophageal inflammation and symptoms of dysphagia in patients with eosinophilic esophagitis. In some embodiments, the question for determining whether the patient avoided solid food is: Since you woke up this morning, did you eat solid food? In further embodiments, the answer options for the question for determining whether the patient avoided solid food comprise: Yes and No. In some embodiments, the question for determining whether the patient had difficulty swallowing solid food is: Since you woke up this morning, has food gone down slowly or been stuck in your throat or chest? In further embodiments, the answer options for the question for determining whether the patient had difficulty swallowing solid food comprise: Yes and No. In some embodiments, the question for determining what action the patient took to correct or relieve difficulty swallowing food is: For the most difficult time you had swallowing food today (during the past 24 hours), did you have to do anything to make the food go down or to get relief? In further embodiments, the answer options for the question for determining what action the patient took to correct or relieve difficulty swallowing food comprise: No, it got better or cleared up on its own; Yes, I had to drink liquid to get relief; Yes, I had to cough and/or gag to get relief; Yes, I had to vomit to get relief; and Yes, I had to seek medical attention to get relief In some embodiments, the question for determining the amount of pain the patient experienced while swallowing food is: What is the worst pain you had while swallowing food over the past 24 hours? In further embodiments, the answer options for the question for determining the amount of pain the patient experienced while swallowing food comprise: None, I had no pain. Mild; Moderate; Severe; and Very severe. In some embodiments, the method further comprises the step of providing a notification or reminder to the patient to complete a daily patient questionnaire.

In another aspect, the invention encompasses non-transitory computer readable storage media encoded with a computer program including instructions executable by a digital processing device to create a daily patient reporting tool comprising: a software module configured to provide a daily patient questionnaire, said questionnaire comprising: a question for determining whether the patient avoided solid food; a question for determining whether the patient had difficulty swallowing solid food; contingent on an affirmative answer to said question for determining whether the patient had difficulty swallowing solid food, a question for determining what action the patient took to correct or relieve difficulty swallowing food; a question for determining the amount of pain the patient experienced while swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia. In some embodiments, the patient has dysphagia associated with eosinophilic esophagitis. In some embodiments, the questionnaire is self-administered by said patient. In some embodiments, the patient is 12 to 45 years old. In some embodiments, the therapy comprises diet intervention therapy. In some embodiments, the therapy comprises pharmacologic therapy. In some embodiments, the therapy comprises immunotherapy. In further embodiments, the therapy comprises corticosteroid therapy. In still further embodiments, the therapy comprises oral administration of budesonide. In some embodiments, the therapy comprises mechanical dilation. In some embodiments, the algorithm incorporates symptom severity data. In some embodiments, the algorithm incorporates symptom frequency data. In some embodiments, the algorithm is optionally corrected for variations in patient compliance with completing a daily patient questionnaire. In some embodiments, the score is a daily average score. In further embodiments, the daily average score is determined over one week. In further embodiments, the daily average score is determined over more than one week. In some embodiments, the score illustrates one or more selected from the group consisting of: (1) severity, intensity, or frequency of patient dysphagia associated with eosinophilic esophagitis; (2) suitability of a patient for a particular diagnostic tool, diagnostic method, or therapy for dysphagia associated with eosinophilic esophagitis; and (3) efficacy of a particular therapy for dysphagia associated with eosinophilic esophagitis. In some embodiments, the score illustrates suitability of a patient for inclusion in a clinical trial. In some embodiments, the score illustrates a patient's compliance in a clinical trial. In some embodiments, the score illustrates reduction in esophageal inflammation and symptoms of dysphagia in patients with eosinophilic esophagitis. In some embodiments, the question for determining whether the patient avoided solid food is: Since you woke up this morning, did you eat solid food? In further embodiments, the answer options for the question for determining whether the patient avoided solid food comprise: Yes and No. In some embodiments, the question for determining whether the patient had difficulty swallowing solid food is: Since you woke up this morning, has food gone down slowly or been stuck in your throat or chest? In further embodiments, the answer options for the question for determining whether the patient had difficulty swallowing solid food comprise: Yes and No. In some embodiments, the question for determining what action the patient took to correct or relieve difficulty swallowing food is: For the most difficult time you had swallowing food today (during the past 24 hours), did you have to do anything to make the food go down or to get relief? In further embodiments, the answer options for the question for determining what action the patient took to correct or relieve difficulty swallowing food comprise: No, it got better or cleared up on its own; Yes, I had to drink liquid to get relief; Yes, I had to cough and/or gag to get relief; Yes, I had to vomit to get relief; and Yes, I had to seek medical attention to get relief In some embodiments, the question for determining the amount of pain the patient experienced while swallowing food is: What is the worst pain you had while swallowing food over the past 24 hours? In further embodiments, the answer options for the question for determining the amount of pain the patient experienced while swallowing food comprise: None, I had no pain. Mild; Moderate; Severe; and Very severe. In some embodiments, the daily patient reporting tool further comprises a software module configured to provide a notification or reminder to said patient to complete said daily patient questionnaire. In further embodiments, the notification or reminder is an audible alarm, visual alert, email, SMS, MMS, phone call, voice mail, blog post, microblog post, social network post, instant message, or combination thereof. In some embodiments, the daily patient reporting tool further comprises a software module configured to communicate patient answers to a centralized database.

In another aspect, the invention encompasses computer-based systems comprising: a digital processing device comprising an operating system configured to perform executable instructions and a memory device; a computer program including instructions executable by the digital processing device to create a daily patient reporting tool comprising: a software module configured to provide a daily patient questionnaire, said questionnaire comprising: a question for determining whether the patient avoided solid food; a question for determining whether the patient had difficulty swallowing solid food; contingent on an affirmative answer to said question for determining whether the patient had difficulty swallowing solid food, a question for determining what action the patient took to correct or relieve difficulty swallowing food; a question for determining the amount of pain the patient experienced while swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia. In some embodiments, the patient has dysphagia associated with eosinophilic esophagitis. In some embodiments, the questionnaire is self-administered by said patient. In some embodiments, the patient is 12 to 45 years old. In some embodiments, the therapy comprises diet intervention therapy. In some embodiments, the therapy comprises pharmacologic therapy. In some embodiments, the therapy comprises immunotherapy. In further embodiments, the therapy comprises corticosteroid therapy. In still further embodiments, the therapy comprises oral administration of budesonide. In some embodiments, the therapy comprises mechanical dilation. In some embodiments, the algorithm incorporates symptom severity data. In some embodiments, the algorithm incorporates symptom frequency data. In some embodiments, the algorithm is optionally corrected for variations in patient compliance with completing a daily patient questionnaire. In some embodiments, the score is a daily average score. In further embodiments, the daily average score is determined over one week. In further embodiments, the daily average score is determined over more than one week. In some embodiments, the score illustrates one or more selected from the group consisting of: (1) severity, intensity, or frequency of patient dysphagia associated with eosinophilic esophagitis; (2) suitability of a patient for a particular diagnostic tool, diagnostic method, or therapy for dysphagia associated with eosinophilic esophagitis; and (3) efficacy of a particular therapy for dysphagia associated with eosinophilic esophagitis. In some embodiments, the score illustrates suitability of a patient for inclusion in a clinical trial. In some embodiments, the score illustrates a patient's compliance in a clinical trial. In some embodiments, the score illustrates reduction in esophageal inflammation and symptoms of dysphagia in patients with eosinophilic esophagitis. In some embodiments, the question for determining whether the patient avoided solid food is: Since you woke up this morning, did you eat solid food? In further embodiments, the answer options for the question for determining whether the patient avoided solid food comprise: Yes and No. In some embodiments, the question for determining whether the patient had difficulty swallowing solid food is: Since you woke up this morning, has food gone down slowly or been stuck in your throat or chest? In further embodiments, the answer options for the question for determining whether the patient had difficulty swallowing solid food comprise: Yes and No. In some embodiments, the question for determining what action the patient took to correct or relieve difficulty swallowing food is: For the most difficult time you had swallowing food today (during the past 24 hours), did you have to do anything to make the food go down or to get relief? In further embodiments, the answer options for the question for determining what action the patient took to correct or relieve difficulty swallowing food comprise: No, it got better or cleared up on its own; Yes, I had to drink liquid to get relief; Yes, I had to cough and/or gag to get relief; Yes, I had to vomit to get relief; and Yes, I had to seek medical attention to get relief In some embodiments, the question for determining the amount of pain the patient experienced while swallowing food is: What is the worst pain you had while swallowing food over the past 24 hours? In further embodiments, the answer options for the question for determining the amount of pain the patient experienced while swallowing food comprise: None, I had no pain. Mild; Moderate; Severe; and Very severe. In some embodiments, the daily patient reporting tool further comprises a software module configured to provide a notification or reminder to said patient to complete said daily patient questionnaire. In further embodiments, the notification or reminder is an audible alarm, visual alert, email, SMS, MMS, phone call, voice mail, blog post, microblog post, social network post, instant message, or combination thereof. In some embodiments, the daily patient reporting tool further comprises a software module configured to communicate patient answers to a centralized database. In some embodiments, the digital processing device is a mobile device. In some embodiments, the computer program is a mobile application.

In another aspect, the invention encompasses methods comprising the steps of: providing a daily patient questionnaire, said questionnaire comprising: a question for determining whether the patient had difficulty swallowing solid food; a question for determining what action the patient took to correct or relieve difficulty swallowing food; and applying an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

In another aspect, the invention encompasses non-transitory computer readable storage media encoded with a computer program including instructions executable by a digital processing device to create a daily patient reporting tool comprising: a software module configured to provide a daily patient questionnaire, said questionnaire comprising: a question for determining whether the patient had difficulty swallowing solid food; a question for determining what action the patient took to correct or relieve difficulty swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

In another aspect, the invention encompasses computer-based systems comprising: a digital processing device comprising an operating system configured to perform executable instructions and a memory device; a computer program including instructions executable by the digital processing device to create a daily patient reporting tool comprising: a software module configured to provide a daily patient questionnaire, said questionnaire comprising: a question for determining whether the patient had difficulty swallowing solid food; a question for determining what action the patient took to correct or relieve difficulty swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

BRIEF DESCRIPTION OF THE FIGURES

FIG. 12 depicts a paper-based 3-question Dysphagia Symptom Questionnaire converted to an electronic format for a 30-day field trial with EoE patients of Example 1.

FIG. 20 illustrates another non-limiting example of a process flow for an algorithm for calculating a dysphagia symptom score.

FIG. 21 depicts a paper-based 4-question Dysphagia Symptom Questionnaire converted to an electronic format for the clinical study of Example 2.

DETAILED DESCRIPTION OF THE INVENTION

Figure 1:
FIGS. 1-3 illustrate a non-limiting example of a mobile application for providing a daily patient dysphagia symptom questionnaire; in this case, a mobile application including patient instructions for completing a questionnaire in the form of a daily diary.

The invention encompasses computer-implemented methods, non-transitory computer-readable storage media encoded with computer programs, and computer-based systems for assessing dysphagia symptoms in patients via a daily patient questionnaire. Advantages of the methods, software, and systems described herein include, but are not limited to, improved convenience for patients, reduction in respondent errors, and elimination of difficulty in symptom recall, all of which improve the accuracy and usefulness of the tool in assessing, for example, severity, intensity, or frequency of patient dysphagia; suitability of a patient for a particular diagnostic tool, diagnostic method, or therapy for dysphagia; efficacy of a particular therapy for dysphagia; suitability of a patient for inclusion in a clinical trial; and/or compliance of a patient in a clinical trial.

In some embodiments, the invention encompasses methods comprising the steps of: providing a daily patient questionnaire, said questionnaire comprising: a question for determining whether the patient avoided solid food; a question for determining whether the patient had difficulty swallowing solid food; contingent on an affirmative answer to said question for determining whether the patient had difficulty swallowing solid food, a question for determining what action the patient took to correct or relieve difficulty swallowing food; a question for determining the amount of pain the patient experienced while swallowing food; and applying an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

In some embodiments, the invention encompasses non-transitory computer readable storage media encoded with a computer program including instructions executable by a digital processing device to create a daily patient reporting tool comprising: a software module configured to provide a daily patient questionnaire, said questionnaire comprising: a question for determining whether the patient avoided solid food; a question for determining whether the patient had difficulty swallowing solid food; contingent on an affirmative answer to said question for determining whether the patient had difficulty swallowing solid food, a question for determining what action the patient took to correct or relieve difficulty swallowing food; a question for determining the amount of pain the patient experienced while swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

In some embodiments, the invention encompasses computer-based systems comprising: a digital processing device comprising an operating system configured to perform executable instructions and a memory device; a computer program including instructions executable by the digital processing device to create a daily patient reporting tool comprising: a software module configured to provide a daily patient questionnaire, said questionnaire comprising: a question for determining whether the patient avoided solid food;

a question for determining whether the patient had difficulty swallowing solid food; contingent on an affirmative answer to said question for determining whether the patient had difficulty swallowing solid food, a question for determining what action the patient took to correct or relieve difficulty swallowing food; a question for determining the amount of pain the patient experienced while swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

In some embodiments, the invention encompasses methods comprising the steps of: providing a daily patient questionnaire, said questionnaire comprising: a question for determining whether the patient had difficulty swallowing solid food; a question for determining what action the patient took to correct or relieve difficulty swallowing food; and applying an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

In some embodiments, the invention encompasses non-transitory computer readable storage media encoded with a computer program including instructions executable by a digital processing device to create a daily patient reporting tool comprising: a software module configured to provide a daily patient questionnaire, said questionnaire comprising: a question for determining whether the patient had difficulty swallowing solid food; a question for determining what action the patient took to correct or relieve difficulty swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

In some embodiments, the invention encompasses computer-based systems comprising: a digital processing device comprising an operating system configured to perform executable instructions and a memory device; a computer program including instructions executable by the digital processing device to create a daily patient reporting tool comprising: a software module configured to provide a daily patient questionnaire, said questionnaire comprising: a question for determining whether the patient had difficulty swallowing solid food; a question for determining what action the patient took to correct or relieve difficulty swallowing food; and a software module configured to apply an algorithm to answers to one or more of said questions to determine a score, wherein said score illustrates one or more selected from the group consisting of: (1) severity, intensity, or frequency of patient dysphagia; (2) suitability of a patient for a particular diagnostic tool, diagnostic method, or therapy for dysphagia; and (3) efficacy of a particular therapy for dysphagia.

Certain Definitions

As used herein, "dysphagia" refers to difficulty with swallowing food or liquid, the sensation of food or liquid passing slowly, or food hanging up, sticking in, or obstructing the esophagus.

As used herein, "vomiting" refers to the process of expelling food or liquid from the mouth; this may or may not be forceful (e.g., projectile vomiting vs. spitting up in very young children).

As used herein, "coping behaviors" may be behaviors used to avoid or lessen dysphagia symptoms. Such behaviors may include: taking medication (other than study medication), taking antacids, cutting food into small pieces, eating less than normal amounts of food, coughing, gagging, vomiting, taking a drink, chewing food longer than normal, avoiding certain foods, seeking medical attention, etc.

As used herein, "immunotherapy" refers to treatment of a condition or disease by modulating, inducing, enhancing, or suppressing an immune response.

As used herein, "medical attention" refers to any assessment, evaluation, treatment, therapy, or intervention overseen or administered by any healthcare provider, including but not limited to, first responders (e.g., emergency medical technician, paramedic, fire fighter, police officer, etc.), physicians, physician assistants, advanced practice registered nurses, nurse practitioners, registered nurses, licensed practical nurses, clinical nurse specialists, and the like.

Patients

In some embodiments, the methods, software, and systems described herein comprise a daily patient reporting tool to assess dysphagia symptoms. In further embodiments, a daily patient reporting tool described herein comprises a software module configured to provide a patient with a daily questionnaire.

A daily patient questionnaire described herein is suitable for a wide range of patients. In some embodiments, the patient is an adult or the patient is 18 or more years old, 21 or more years old, 25 or more years old, 30 or more years old, 35 or more years old, 40 or more years old, 45 or more years old, 50 or more years old, 55 or more years old, 60 or more years old, 65 or more years old, 70 or more years old, 75 or more years old, or 80 or more years old. In some embodiments, a patient is 18-21 years old, 21-30 years old, 31-40 years old, 41-50 years old, 51-60 years old, 61-70 years old, 71-80 years old, or 81-90 years old. In other embodiments, the individual is an adolescent or the patient is 12-18 years old. In further embodiments, a patient is 12-17 years old, 12-16 years old, 12-15 years old, 12-14 years old, 12-13 years old, 13-18 years old, 14-18 years old, 15-18 years old, 16-18 years old, or 17-18 years old. In still further embodiments, a patient is 12, 13, 14, 15, 16, 17, or 18 years old. In yet other embodiments, the individual is a child or the patient is 1-12 years old. In further embodiments, a patient is 1-11 years old, 1-10 years old, 1-9 years old, 1-8 years old, 1-7 years old, 1-6 years old, 1-5 years old, 1-4 years old, 1-3 years old, 1-2 years old, 2-12 years old, 3-12 years old, 4-12 years old, 5-12 years old, 6-12 years old, 7-12 years old, 8-12 years old, 9-12 years old, 10-12 years old, or 11-12 years old. In still further embodiments, a patient is 1, 2, 3, 4, 5, 6, 7, 8, 9, 10, 11, or 12 years old. In yet other embodiments, the individual is an infant or the patient is 1-12 months old. In further embodiments, a patient is 1, 2, 3, 4, 5, 6, 7, 8, 9, 10, 11, or 12 months old.

A daily patient questionnaire described herein is optionally adjusted or tuned to suit the characteristics of a particular patient or group of patients. In some embodiments, a patient is evaluated to determine, for example, developmental age and/or language skills such as language proficiency, language comprehension skills, and reading comprehension skills. In some embodiments, the wording of a daily patient questionnaire described herein is optionally modified to accommodate a particular patient's characteristics such as age and/or language skills.

A daily patient questionnaire described herein is suitably administered in a variety of ways. In some embodiments, a questionnaire is self-administered by a patient. In other embodiments, a questionnaire is administered by a caregiver such as a friend or family member. In yet other embodiments, a questionnaire is administered by a healthcare provider such as, by way of non-limiting examples, a physician, a nurse practitioner, a physician's assistant, a registered nurse, a licensed vocational nurse, a hospice worker, or a medical technician. In some embodiments, a daily patient questionnaire is administered on a daily basis by a combination of those individuals described herein. In further embodiments, a patient questionnaire is in the form of a daily diary kept by a patient.

A daily patient questionnaire described herein is suitably administered to a patient with dysphagia. In some embodiments, dysphagia means difficulty with swallowing food or liquid, the sensation of food or liquid passing slowly, or food hanging up, sticking in, or obstructing the esophagus. In further embodiments, dysphagia refers to esophageal dysphagia rather than oropharyngeal dysphagia or functional dysphagia. In various embodiments, a patient has a wide range of severity of dysphagia. By way of non-limiting examples, in various embodiments, a patient has mild dysphagia, moderate dysphagia, and severe dysphagia. A patient may have persistent or intermittent dysphagia, and the dysphagia may remit and relapse in a cyclical fashion.

In various embodiments, a daily patient questionnaire described herein is suitably administered to a patient with dysphagia associated with, by way of non-limiting examples, cerebrovascular stroke, multiple sclerosis, myasthenia gravis, Parkinson's disease and Parkinsonism syndromes, amyotrophic lateral sclerosis, Bell's palsy, bulbar palsy, pseudobulbar palsy, xerostomia, radiation exposure, neck malignancies, neurotoxins (e.g., snake venom, etc.), pharyngitis, achalasia, peptic esophagitis, carcinoma of the esophagus, carcinoma of the gastric cardia, external compression of the esophagus, candida esophagitis, pharyngeal pouch, esophageal web, esophageal leiomyoma, and systemic sclerosis. In some embodiments, a patient has dysphagia associated with eosinophilic esophagitis.

In various embodiments, a daily patient questionnaire described herein is suitably administered to a patient in various stages of diagnosis and/or treatment for dysphagia. In some embodiments, a patient is not diagnosed with dysphagia or a condition associated with dysphagia. In other embodiments, a patient has been diagnosed with dysphagia or a condition associated with dysphagia. In some embodiments, a patient is undergoing assessment of the severity, intensity, and/or frequency of their dysphagia symptoms. In some embodiments, a patient is not undergoing therapy (e.g., treatment) for dysphagia or a condition associated with dysphagia. In some embodiments, a patient is undergoing therapy for dysphagia or a condition associated with dysphagia. In further embodiments, a patient is undergoing assessment of the severity, intensity, and/or frequency of dysphagia symptoms to assess the efficacy of a therapy for dysphagia. In some embodiments, a patient's suitability for inclusion in a clinical trial is being evaluated. In some embodiments, a patient's compliance with a procedure or regimen in a clinical trial is being evaluated. In further embodiments, a clinical trial is for a diagnostic tool, diagnostic method, or therapy for dysphagia or a condition associated with dysphagia.

Daily Questionnaire

Figure 2:
Figure 3:
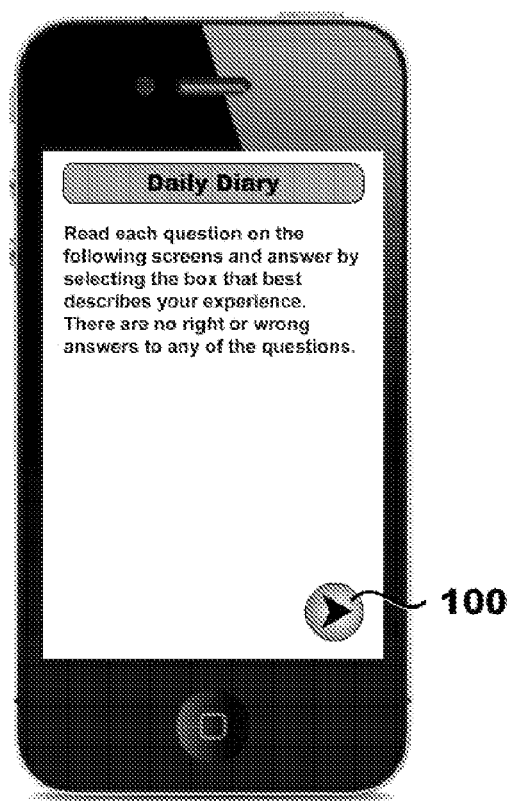

Referring to FIGS. 1-3, in a particular embodiment, a daily patient reporting tool includes a daily patient questionnaire that includes patient instructions. In further embodiments, a GUI element (e.g., a button, link, icon, etc.) 100 allows a patient to navigate through a series of instructions prior to completing a daily patient questionnaire. In still further embodiments, patient instructions include information pertaining to, by way of non-limiting examples, the purpose of the tool and questionnaire, what to expect when participating in the questionnaire, when to participate in the questionnaire, how to participate in the questionnaire, and the like.

In some embodiments, a daily patient reporting tool includes a daily patient questionnaire to assess dysphagia symptoms. A daily patient questionnaire suitably has a wide range of lengths and numbers of questions. In various embodiments, a daily patient questionnaire comprises, by way of non-limiting examples, 1, 2, 3, 4, 5, 6, 7, 8, 9, 10, 11, 12, 13, 14, 15, 16, 17, 18, 19, and 20 or more questions. Accordingly, a daily patient questionnaire suitably requires a wide range of time to complete. In various embodiments, a daily patient questionnaire requires, by way of non-limiting examples, 1, 2, 3, 4, 5, 6, 7, 8, 9, 10, 11, 12, 13, 14, 15, 16, 17, 18, 19, 20, 30, 40, 50, 60 or more seconds to complete, including increments therein. In further various embodiments, a daily patient questionnaire requires, by way of non-limiting examples, 1, 2, 3, 4, 5, 6, 7, 8, 9, 10, 11, 12, 13, 14, 15, 16, 17, 18, 19, 20 or more minutes to complete. Because convenience is a factor in patient participation and compliance, in some embodiments, a number of questions and/or a time to complete are selected, in part, to facilitate a convenient patient experience.

In some embodiments, a daily patient reporting tool includes a daily patient questionnaire designed for patient participation during a particular time of day. In various embodiments, a daily patient questionnaire designed for patient participation, for example, upon waking in the morning, before the first meal of the day, after the first meal of the day, before the second meal of the day, after the second meal of the day, before the last meal of the day, after the last meal of the day, before going to sleep at night, and the like. In some embodiments, a daily patient questionnaire designed for patient participation after the last meal of the day.

In some embodiments, a daily patient reporting tool includes a daily patient questionnaire that comprises a plurality of items adapted to elicit input from a patient. Many types of items are suitable to elicit appropriate responses including, by way of non-limiting examples, text-based questions, audio questions, video questions, and graphical questions (e.g., pictograms, etc.). In some embodiments, the items are text-based questions.

In some embodiments, a daily patient reporting tool includes a daily patient questionnaire that comprises a plurality of questions. In some embodiments, questions are presented in a linear progression. In other embodiments, questions are presented in a non-linear progression. In further embodiments, questions are presented in a branching progression, wherein the presentation of one or more questions is based, in part or in whole, on a patient answer to one or more previous questions. In still further embodiments, presentation or one or more questions is contingent (e.g., conditional) on a particular patient answer to a previous question.

In some embodiments, a daily patient reporting tool includes a daily patient questionnaire that comprises a question for determining whether the patient avoided food. In further embodiments, a question for determining whether the patient avoided food is directed to avoidance of solid food. In further embodiments, a question for determining whether the patient avoided food is directed to avoidance of semi-solid food. In further embodiments, a question for determining whether the patient avoided food is directed to avoidance of liquids. In still further embodiments, a question for determining whether the patient avoided food is directed to avoidance of combinations of the types of foods disclosed herein. In further embodiments, a question for determining whether the patient avoided food is useful for discerning patient avoidance from absence of symptoms. By way of non-limiting example, a suitable question is: "Since you woke up this morning, did you eat solid food?" Other suitable examples of questions for determining whether the patient avoided solid food include: "Did you eat solid food today?"; "Have you avoided solid food today?"; and, "During the course of the day did you avoid solid food?" By way of non-limiting examples, suitable answer options for a question for determining whether the patient avoided solid food include: "Yes" and "No"; "All the time," "Sometimes," and "No"; "At one meal," "At two meals," "At all meals," and "No."

Figure 4:
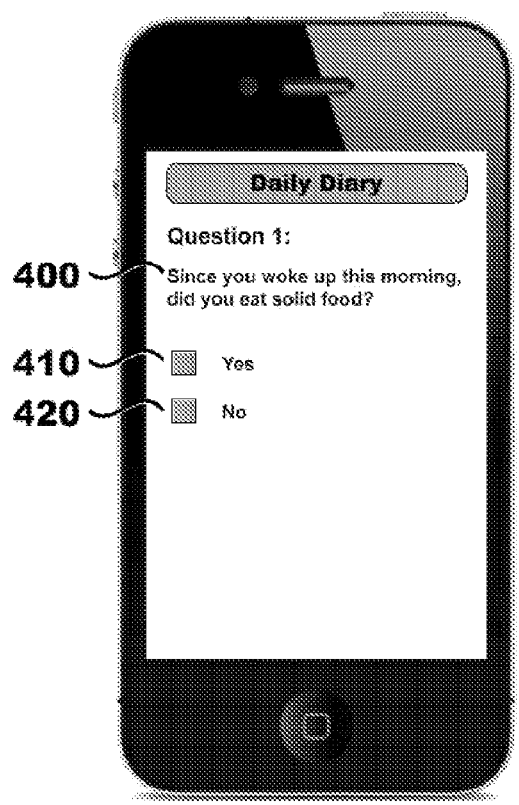
FIG. 4 illustrates a non-limiting example of a mobile application for providing a daily patient dysphagia symptom questionnaire; in this case, a questionnaire including a question regarding avoidance of solid food.

Referring to FIG. 4, in a particular embodiment, a daily patient reporting tool includes a daily patient questionnaire in the form of a daily diary, which is implemented as a mobile application. The questionnaire comprises a question for determining whether the patient avoided solid food. In this embodiment, the question is "Since you woke up this morning, did you eat solid food?" 400. Further, in this embodiment, the answer options are "Yes" 410 and "No" 420.

In some embodiments, a daily patient reporting tool includes a daily patient questionnaire that comprises a question for determining whether the patient had difficulty swallowing food. In further embodiments, a question for determining whether the patient had difficulty swallowing food is directed to swallowing solid food. In further embodiments, a question for determining whether the patient had difficulty swallowing food is directed to swallowing semi-solid food. In further embodiments, a question for determining whether the patient had difficulty swallowing food is directed to swallowing liquids. In still further embodiments, a question for determining whether the patient had difficulty swallowing food is directed to swallowing combinations of the types of foods disclosed herein. By way of non-limiting example, a suitable question is: "Since you woke up this morning, has food gone down slowly or been stuck in your throat or chest?" Other suitable examples of questions for determining whether the patient had difficulty swallowing solid food include: "Did you experience difficulty swallowing solid food today?"; "Has food gone down slowly or been stuck in your throat or chest today?"; and, "During the course of the day, did you have difficulty swallowing solid food?" By way of non-limiting examples, suitable answer options for a question for determining whether the patient had difficulty swallowing solid food include: "Yes" and "No"; "All the time," "Sometimes," and "No"; "At one meal," "At two meals," "At all meals," and "No."

In some embodiments, presentation of a question for determining whether the patient had difficulty swallowing solid food is contingent (e.g., conditional) on a patient's answer to a question for determining whether the patient avoided solid food. In further embodiments, presentation of a question for determining whether the patient had difficulty swallowing solid food is contingent (e.g., conditional) on a patient's negative answer to a question for determining whether the patient avoided solid food.

Figure 5:
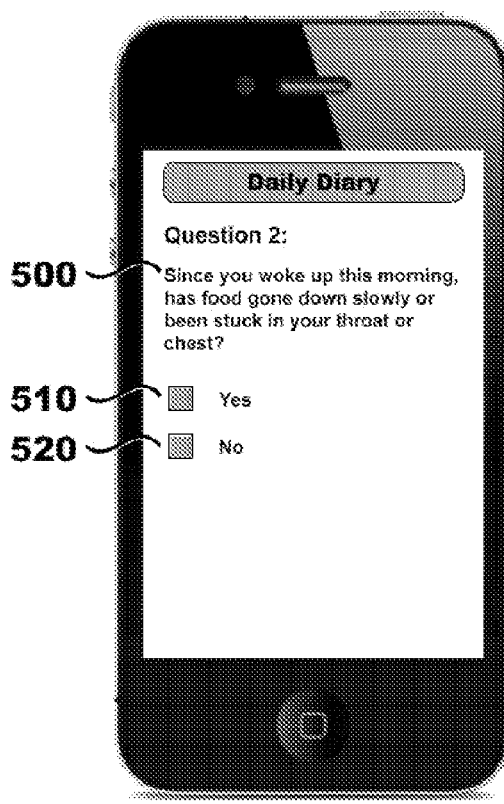
FIG. 5 illustrates a non-limiting example of a mobile application for providing a daily patient dysphagia symptom questionnaire; in this case, a questionnaire including a question regarding difficulty swallowing solid food.

Referring to FIG. 5, in a particular embodiment, a daily patient reporting tool includes a daily patient questionnaire in the form of a daily diary, which is implemented as a mobile application. The questionnaire comprises a question for determining whether the patient had difficulty swallowing solid food. In this embodiment, the question is "Since you woke up this morning, has food gone down slowly or been stuck in your throat or chest?" 500. Further, in this embodiment, the answer options are "Yes" 510 and "No" 520.

In some embodiments, a daily patient reporting tool includes a daily patient questionnaire that comprises a question for determining what action the patient took to correct or relieve difficulty swallowing food. By way of non-limiting example, a suitable question is: "For the most difficult time you had swallowing food today (during the past 24 hours), did you have to do anything to make the food go down or to get relief?" Other suitable examples of questions for determining what action the patient took to correct or relieve difficulty swallowing food include: "At its worst, did you have to take action to get relief from your difficulty swallowing solid food today?"; "Did you have to do anything to overcome the worst of your difficulty swallowing solid food today?"; "During the course of the day, did you have to anything to help solid food go down?" By way of non-limiting examples, suitable answer options for the question comprise: "No, it got better or cleared up on its own"; "Yes, I had to drink liquid to get relief"; "Yes, I had to cough and/or gag to get relief"; "Yes, I had to vomit to get relief"; and, "Yes, I had to seek medical attention to get relief" In some embodiments, suitable answer options for a question for determining what action the patient took to correct or relieve difficulty swallowing food include those asking about patient coping behaviors, including, by way of non-limiting examples, taking medication (e.g., over-the-counter medication, prescription medication, herbal remedies, etc.), taking antacids, cutting food into small pieces, eating less than normal amounts of food, chewing food longer than normal, avoiding certain foods, etc.

In some embodiments, presentation of a question for determining what action the patient took to correct or relieve difficulty swallowing food is contingent (e.g., conditional) on a patient's answer to a question for determining whether the patient had difficulty swallowing solid food. In further embodiments, presentation of a question for determining what action the patient took to correct or relieve difficulty swallowing food is contingent (e.g., conditional) on a patient's affirmative answer to a question for determining whether the patient had difficulty swallowing solid food.

Figure 6:
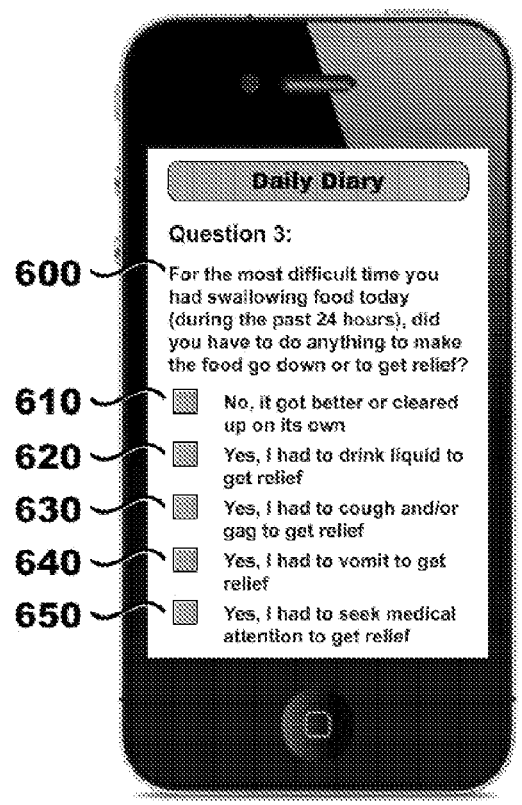
FIG. 6 illustrates a non-limiting example of a mobile application for providing a daily patient dysphagia symptom questionnaire; in this case, a questionnaire including a question regarding action taken to correct or relieve difficulty swallowing food.

Referring to FIG. 6, in a particular embodiment, a daily patient reporting tool includes a daily patient questionnaire in the form of a daily diary, which is implemented as a mobile application. The questionnaire comprises a question for determining what action the patient took to correct or relieve difficulty swallowing food. In this embodiment, the question is "For the most difficult time you had swallowing food today (during the past 24 hours), did you have to do anything to make the food go down or to get relief?" 600. Further, in this embodiment, the answer options are: "No, it got better or cleared up on its own" 610; "Yes, I had to drink liquid to get relief" 620; "Yes, I had to cough and/or gag to get relief" 630; "Yes, I had to vomit to get relief" 640; and, "Yes, I had to seek medical attention to get relief" 650.

In some embodiments, a daily patient reporting tool includes a daily patient questionnaire that comprises a question for determining the amount of pain the patient experienced when swallowing food. By way of non-limiting example, a suitable question is: "What was the worst pain you had while swallowing food over the past 24 hours?" Other suitable examples of questions for determining the amount of pain a patient experienced when swallowing food include: "At its worst, how much pain did you experience when swallowing food today?"; "During the course of the day, how much pain did you experience when swallowing food?" By way of non-limiting examples, suitable answer options for the question comprise: "None, I had no pain"; "Mild"; "Moderate"; "Severe"; and, "Very severe." In some embodiments, suitable answer options for a question for determining the amount of pain a patient experienced when swallowing food include those asking about pain scales, including, by way of non-limiting examples, scale of 1 to 5, scale of 1 to 10, a Likert scale, a linear visual analog scale, etc.

Figure 7:
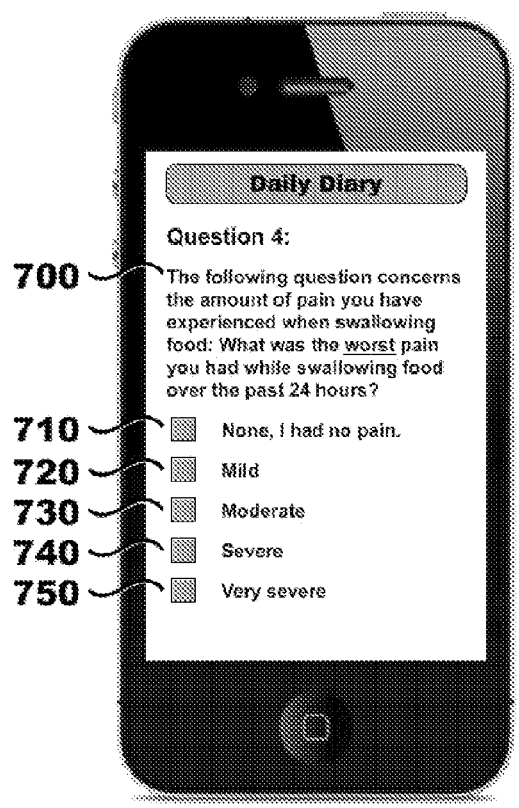
FIG. 7 illustrates a non-limiting example of a mobile application for providing a daily patient dysphagia symptom questionnaire; in this case, a questionnaire including a question regarding pain experienced when swallowing food.

Referring to FIG. 7, in a particular embodiment, a daily patient reporting tool includes a daily patient questionnaire in the form of a daily diary, which is implemented as a mobile application. The questionnaire comprises a question for determining the amount of pain the patient experienced while swallowing food. In this embodiment, the question is "What was the worst pain you had while swallowing food over the past 24 hours?" 700. Further, in this embodiment, the answer options are: "None, I had no pain" 710; "Mild" 720; "Moderate" 730; "Severe" 740; and, "Very severe"750.

Referring to FIGS. 1-7, in some embodiments, the wording of, for example, the instructions, questions, and/or answers in a daily patient questionnaire are customized based on the native language and level of language skill of a representative group of patients. In further embodiments, the customized wording is verified and/or validated by testing patients' comprehension of those specific words.

In some embodiments, a daily patient questionnaire in the form of a daily diary for assessing a patient's dysphagia symptoms includes only a question for assessing a patient's avoidance of solid food (an "avoidance question"). In some embodiments, a daily patient questionnaire in the form of a daily diary for assessing a patient's dysphagia symptoms includes only a question for assessing a patient's frequency of symptoms (a "frequency question"). In some embodiments, a daily patient questionnaire in the form of a daily diary for assessing a patient's dysphagia symptoms includes only a question for assessing a patient's intensity/severity of symptoms as reflected by the patient's response to their symptoms/action taken (a "response question"). In some embodiments, a daily patient questionnaire in the form of a daily diary for assessing a patient's dysphagia symptoms includes only a question for assessing a patient's intensity/severity of symptoms as reflected by the patient's response to their symptoms/action taken (a "pain question").

Many combinations of questions described herein are suitable for a daily patient questionnaire in the form of a daily diary for assessing a patient's dysphagia symptoms. Exemplary question combinations are provided in Table 1.

TABLE 1

Exemplary Question Combinations

| Exemplary daily patient questionnaire | Avoidance Question | Frequency Question | Response Question | Pain Question |
|---|---|---|---|---|
| 1 | x | | | |
| 2 | | x | | |
| 3 | | | x | |
| 4 | | | | x |
| 5 | x | x | x | x |
| 6 | x | x | | |
| 7 | x | | x | |
| 8 | x | | | x |
| 9 | | x | x | |
| 10 | | x | | x |
| 11 | | | x | x |

In some embodiments, a daily patient questionnaire in the form of a daily diary for assessing a patient's dysphagia symptoms includes only one question. In further embodiments, a daily patient questionnaire an avoidance question as described herein. In further embodiments, a daily patient questionnaire a frequency question as described herein. In further embodiments, a daily patient questionnaire a response question as described herein. In further embodiments, a daily patient questionnaire a pain question as described herein.

In some embodiments, a daily patient questionnaire in the form of a daily diary for assessing a patient's dysphagia symptoms includes only two questions. In further embodiments, a daily patient questionnaire includes avoidance and frequency questions as described herein. In further embodiments, a daily patient questionnaire includes avoidance and response questions as described herein. In further embodiments, a daily patient questionnaire includes avoidance and pain questions as described herein. In further embodiments, a daily patient questionnaire includes frequency and response questions as described herein. In further embodiments, a daily patient questionnaire includes frequency and pain questions as described herein. In further embodiments, a daily patient questionnaire includes response and pain questions as described herein.

In some embodiments, a daily patient questionnaire in the form of a daily diary for assessing a patient's dysphagia symptoms includes only three questions. In further embodiments, a daily patient questionnaire includes avoidance, frequency, and response questions as described herein. In further embodiments, a daily patient questionnaire includes avoidance, frequency, and pain questions as described herein. In further embodiments, a daily patient questionnaire includes frequency, response, and pain questions as described herein. In further embodiments, a daily patient questionnaire includes avoidance, response, and pain questions as described herein.

In some embodiments, a daily patient questionnaire in the form of a daily diary for assessing a patient's dysphagia symptoms includes avoidance, frequency, response, and pain questions described herein.

Many graphic user interface (GUI) elements are suitable for allowing a patient to participate in a questionnaire by navigating and answer questions. In various embodiments, suitable GUI elements include, by way of non-limiting examples, text, links, buttons, icons, illustrations, photographs, and avatars. In some embodiments, suitable GUI elements are form elements including, by way of non-limiting examples, checkboxes, radio buttons, text fields, and drop-down menus. In some embodiments, suitable GUI elements are interactive multimedia elements including, by way of non-limiting examples, sliders, dials, audio files, video files, games, and the like.

In some embodiments, a patient answers questions by using a pointing device including, by way of non-limiting examples, a mouse, trackball, trackpad, joystick, pen, or stylus. In further embodiments, a patient uses a pointing device to roll over, hover over, click, double click, highlight, or otherwise indicate or activate a GUI element. In some embodiments, a patient answers questions by using a touch screen display or multi-touch screen display. In further embodiments a patient uses a touch screen display or multi-touch screen display to touch, tap, double tap, swipe, pinch, highlight, or otherwise indicate or activate a GUI element. In some embodiments, a patient answers questions by using a keyboard, keypad, or alternative text input device. In further embodiments a patient uses a text input device to enter text or numbers. In other embodiments, a patient answers questions by using a microphone to capture voice or other sound input. In other embodiments, a patient answers questions by using a video camera to capture motion or visual input.

A daily patient questionnaire described herein is suitably presented in a wide range of languages. In various embodiments, a daily patient reporting tool includes a daily patient questionnaire in a language selected from a group including, by way of non-limiting examples, English, Spanish, Italian, Portuguese, French, Dutch, Polish, German, Russian, Ukrainian, Mandarin, Wu, Cantonese, Hindi, Punjabi, Bengali, Marathi, Urdu, Arabic, Turkish, Tamil, Farsi, Japanese, Korean, Vietnamese, Thai, Burmese, Malay, Telugu, Javanese, Tagalog, and dialects thereof.

Particular Daily Patient Questionnaire Embodiment

In a particular embodiment, a daily patient reporting tool includes a daily patient questionnaire that comprises a first question for determining whether the patient avoided solid food; namely, "Since you woke up this morning, did you eat solid food?" In this embodiment, answer options for a first question comprise "Yes" and "No." See, e.g., FIG. 4.

In a particular embodiment, a daily patient reporting tool includes a daily patient questionnaire that comprises a second question for determining whether the patient had difficulty swallowing solid food; namely, "Since you woke up this morning, has food gone down slowly or been stuck in your throat or chest?" In this embodiment, answer options for a second question comprise "Yes" and "No." See, e.g., FIG. 5.

In a particular embodiment, a daily patient reporting tool includes a daily patient questionnaire that comprises a third question for determining what action the patient took to correct or relieve difficulty swallowing food; namely, "For the most difficult time you had swallowing food today (during the past 24 hours), did you have to do anything to make the food go down or to get relief?" In this embodiment, answer options for a third question comprise: "No, it got better or cleared up on its own"; "Yes, I had to drink liquid to get relief"; "Yes, I had to cough and/or gag to get relief"; "Yes, I had to vomit to get relief"; and, "Yes, I had to seek medical attention to get relief." See, e.g., FIG. 6.

In a particular embodiment, a daily patient reporting tool includes a daily patient questionnaire that comprises a fourth question for determining the amount of pain a patient experienced when swallowing food; namely, "What was the worst pain you had while swallowing food over the past 24 hours?" In this embodiment, answer options for a fourth question comprise "None, I had no pain," "Mild," "Moderate," "Severe," and "Very severe." See, e.g., FIG. 7.

Particular Daily Patient Questionnaire Embodiment

In a particular embodiment, a daily patient reporting tool includes a daily patient questionnaire that comprises a first question for determining whether the patient had difficulty swallowing solid food; namely, "Since you woke up this morning, has food gone down slowly or been stuck in your throat or chest?" In this embodiment, answer options for a first question comprise "Yes" and "No." See, e.g., FIG. 5.

In a particular embodiment, a daily patient reporting tool includes a daily patient questionnaire that comprises a second question for determining what action the patient took to correct or relieve difficulty swallowing food; namely, "For the most difficult time you had swallowing food today (during the past 24 hours), did you have to do anything to make the food go down or to get relief?" In this embodiment, answer options for a second question comprise: "No, it got better or cleared up on its own"; "Yes, I had to drink liquid to get relief"; "Yes, I had to cough and/or gag to get relief"; "Yes, I had to vomit to get relief"; and, "Yes, I had to seek medical attention to get relief" See, e.g., FIG. 6.

Algorithm

In some embodiments, a daily patient reporting tool includes a software module configured to apply an algorithm to one or more patient answers to a questionnaire to determine a score. In some embodiments a score is a dysphagia-free score. In further embodiments, a score indicates freedom of dysphagia symptoms (e.g., a dysphagia symptom-free score). In still further embodiments, a score indicates, for example, a number of days without dysphagia or dysphagia symptoms, a percentage of days without dysphagia or dysphagia symptoms, and/or a number of consecutive days without dysphagia or dysphagia symptoms within any give time interval. In some embodiments a score is a dysphagia score. In further embodiments, a score indicates severity of dysphagia symptoms and/or frequency of dysphagia symptoms (e.g., a dysphagia symptom score). In some embodiments, an algorithm comprises numeric elements assigned to each answer option to one or more questions of a questionnaire. In further embodiments, higher numbers are assigned to answer options indicating more severe dysphagia symptoms. In still further embodiments, a daily score is the sum of the numeric elements for the selected answer option for each question. In some embodiments, patient answers to one or more questions of a questionnaire are collected and analyzed, but no numeric elements are assigned.

Figure 8:
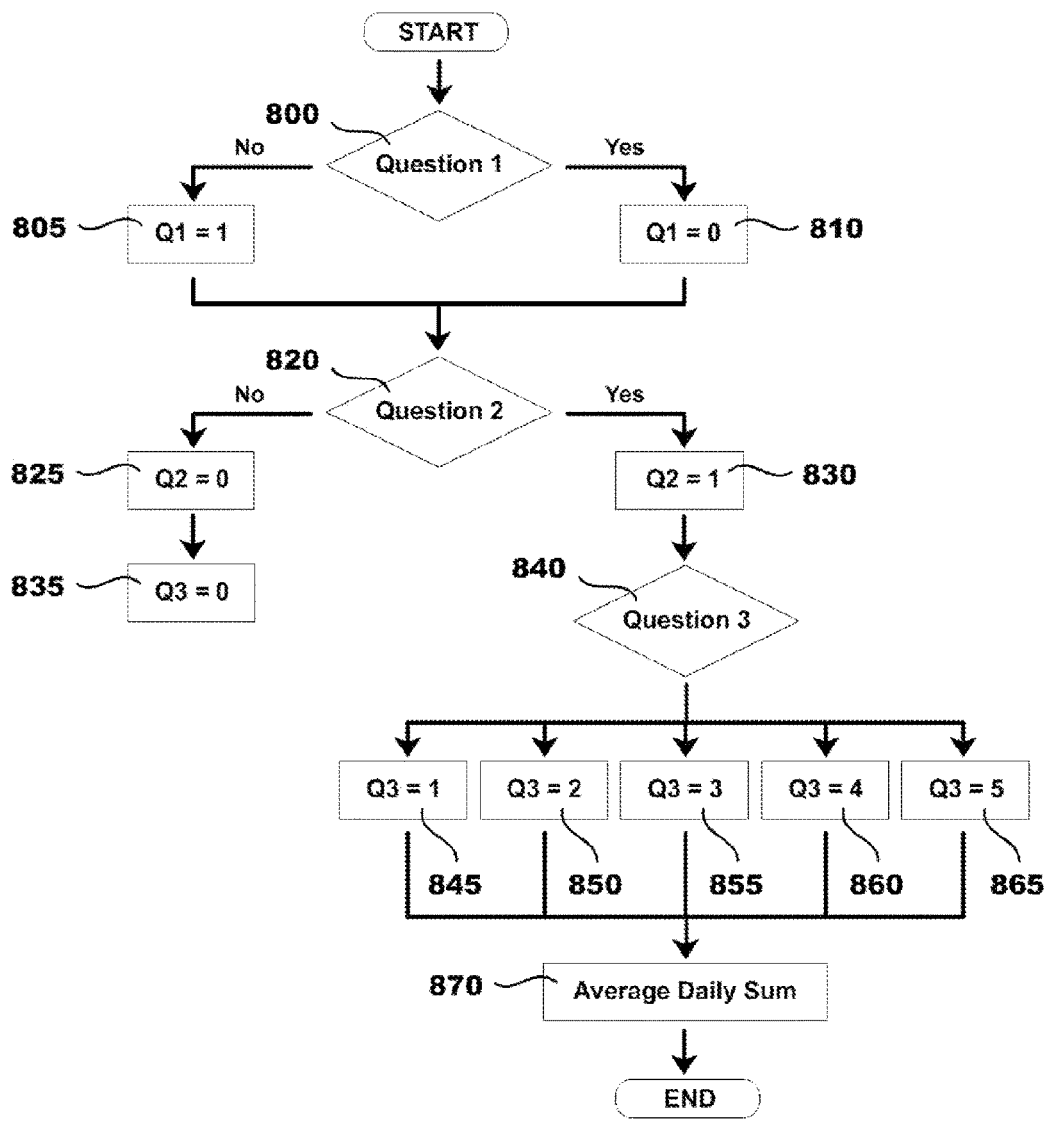
FIG. 8 illustrates a non-limiting example of a process flow for an algorithm for calculating a dysphagia symptom score.

Referring to FIG. 8, in a particular embodiment, a first question is for determining whether the patient avoided solid food 800. An answer option indicating that the patient did not avoid solid food is assigned the numeric element 0 (e.g., Q1=0) 810. An answer option indicating that the patient did avoid solid food is assigned the numeric element 1 (e.g., Q1=1) 805. A second question is for determining whether the patient had difficulty swallowing solid food 820. An answer option indicating that the patient did not have difficulty swallowing solid food is assigned the numeric element 0 (e.g., Q2=0) 825. An answer option indicating that the patient did have difficulty swallowing solid food is assigned the numeric element 1 (e.g., Q2=1) 830. A third question for determining what action the patient took to correct or relieve difficulty swallowing food 840. In this embodiment, display of a third question for determining what action the patient took to correct or relieve difficulty swallowing food 840 is contingent on an affirmative answer to a second question for determining whether the patient had difficulty swallowing solid food 820. Accordingly, in this embodiment, where a patient indicates that they did not have difficulty swallowing solid food, a third question for determining what action the patient took to correct or relieve difficulty swallowing food is automatically assigned the numeric element 0 (e.g., Q3=0) 835. Answer options to a third question for determining what action the patient took to correct or relieve difficulty swallowing food 840 are assigned numeric elements based on the severity of the action. In this embodiment, an answer option indicating that the patient did not have to take action is assigned the numeric element 1 (e.g., Q3=1) 845. An answer option indicating that the patient had to drink liquid is assigned the numeric element 2 (e.g., Q3=2) 850 An answer option indicating that the patient had to cough and/or gag is assigned the numeric element 3 (e.g., Q3=3) 855. An answer option indicating that the patient had to vomit is assigned the numeric element 4 (e.g., Q3=4) 860. An answer option indicating that the patient had to seek medical attention is assigned the numeric element 5 (e.g., Q3=5) 865. A daily score in this case is Q1+Q2+Q3 870.

Figure 9:
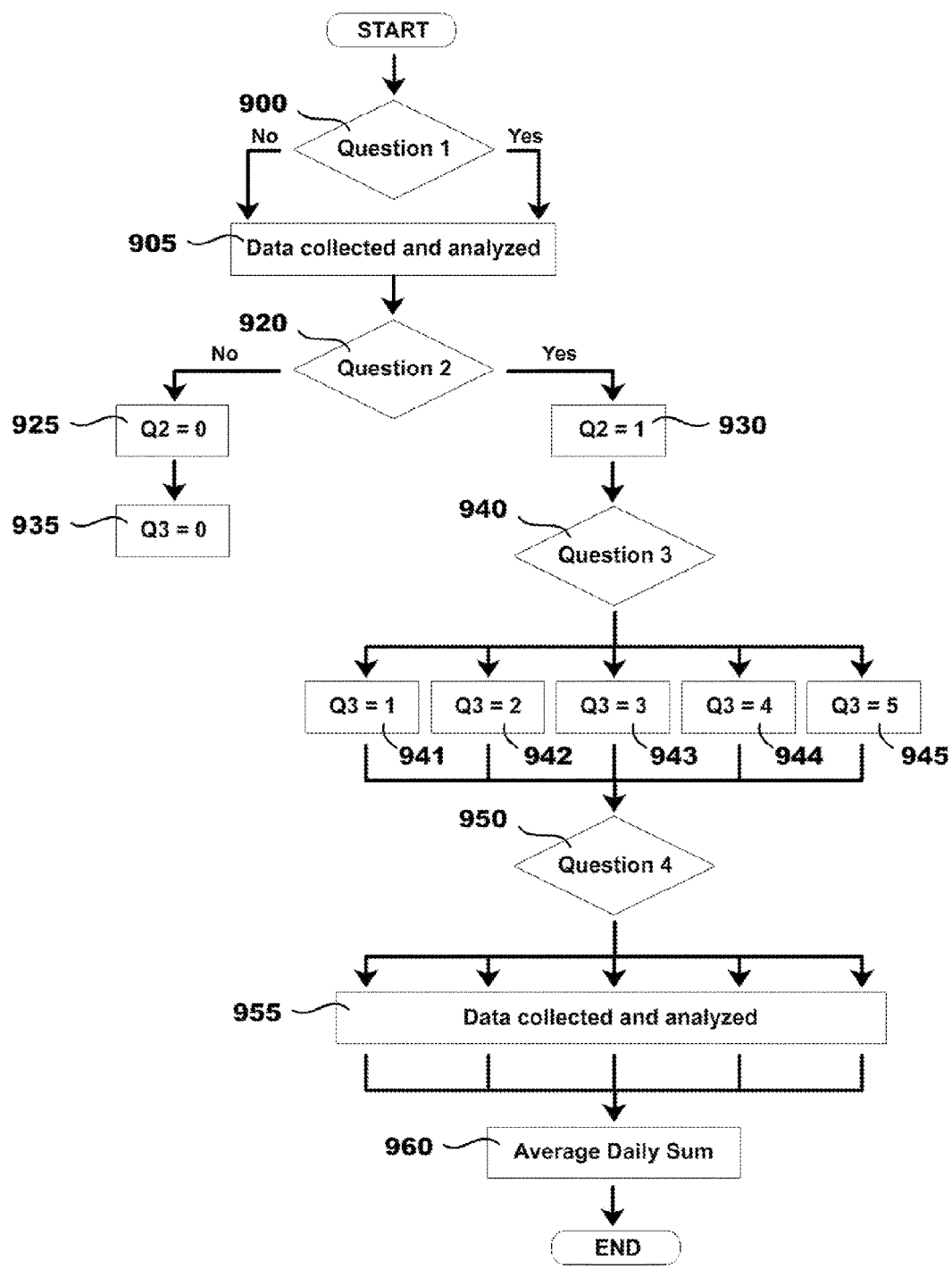
FIG. 9 illustrates another non-limiting example of a process flow for an algorithm for calculating a dysphagia symptom score.

Referring to FIG. 9, in a particular embodiment, a first question is for determining whether the patient avoided solid food 900. Answer options indicating whether or not the patient avoided solid food are collected and analyzed, but not assigned numeric elements 905. A second question is for determining whether the patient had difficulty swallowing solid food 920. An answer option indicating that the patient did not have difficulty swallowing solid food is assigned the numeric element 0 (e.g., Q2=0) 925. An answer option indicating that the patient did have difficulty swallowing solid food is assigned the numeric element 1 (e.g., Q2=1) 930. A third question for determining what action the patient took to correct or relieve difficulty swallowing food 940. In this embodiment, display of a third question for determining what action the patient took to correct or relieve difficulty swallowing food 940 is contingent on an affirmative answer to a second question for determining whether the patient had difficulty swallowing solid food 920. Accordingly, in this embodiment, where a patient indicates that they did not have difficulty swallowing solid food, a third question for determining what action the patient took to correct or relieve difficulty swallowing food is automatically assigned the numeric element 0 (e.g., Q3=0) 935. Answer options to a third question for determining what action the patient took to correct or relieve difficulty swallowing food 940 are assigned numeric elements based on the severity of the action. In this embodiment, an answer option indicating that the patient did not have to take action is assigned the numeric element 1 (e.g., Q3=1) 941. An answer option indicating that the patient had to drink liquid is assigned the numeric element 2 (e.g., Q3=2) 942. An answer option indicating that the patient had to cough and/or gag is assigned the numeric element 3 (e.g., Q3=3) 943. An answer option indicating that the patient had to vomit is assigned the numeric element 4 (e.g., Q3=4) 944. An answer option indicating that the patient had to seek medical attention is assigned the numeric element 5 (e.g., Q3=5) 945. A fourth question for determining the amount of pain a patient experienced when swallowing food 950. Answer options to a fourth question for determining the amount of pain a patient experienced when swallowing food 950 are based on the severity of the pain. In this embodiment, answer options to a fourth question for determining the amount of pain a patient experienced when swallowing food 950 are collected and analyzed, but not assigned numeric elements 955. A daily score in this case is Q2+Q3 960.

Referring to FIG. 20, in a particular embodiment, a first question is for determining whether the patient avoided solid food 2000. Answer options indicating whether or not the patient avoided solid food are collected and analyzed, but not assigned numeric elements 2005. A second question is for determining whether the patient had difficulty swallowing solid food 2020. An answer option indicating that the patient did not have difficulty swallowing solid food is assigned the numeric element 0 (e.g., Q2=0) 2025. An answer option indicating that the patient did have difficulty swallowing solid food is assigned the numeric element 2 (e.g., Q2=2) 2030. A third question for determining what action the patient took to correct or relieve difficulty swallowing food 2040. In this embodiment, display of a third question for determining what action the patient took to correct or relieve difficulty swallowing food 2040 is contingent on an affirmative answer to a second question for determining whether the patient had difficulty swallowing solid food 2020. Accordingly, in this embodiment, where a patient indicates that they did not have difficulty swallowing solid food, a third question for determining what action the patient took to correct or relieve difficulty swallowing food is automatically assigned the numeric element 0 (e.g., Q3=0) 2035. Answer options to a third question for determining what action the patient took to correct or relieve difficulty swallowing food 2040 are assigned numeric elements based on the severity of the action. In this embodiment, an answer option indicating that the patient did not have to take action is assigned the numeric element 0 (e.g., Q3=0) 2041. An answer option indicating that the patient had to drink liquid is assigned the numeric element 1 (e.g., Q3=1) 2042. An answer option indicating that the patient had to cough and/or gag is assigned the numeric element 2 (e.g., Q3=2) 2043. An answer option indicating that the patient had to vomit is assigned the numeric element 3 (e.g., Q3=3) 2044. An answer option indicating that the patient had to seek medical attention is assigned the numeric element 4 (e.g., Q3=4) 2045. A fourth question for determining the amount of pain a patient experienced when swallowing food 2050. Answer options to a fourth question for determining the amount of pain a patient experienced when swallowing food 2050 are based on the severity of the pain. In this embodiment, answer options to a fourth question for determining the amount of pain a patient experienced when swallowing food 2050 are collected and analyzed, but not assigned numeric elements 2055. A daily score in this case is Q2+Q3 2060.

Figure 10:
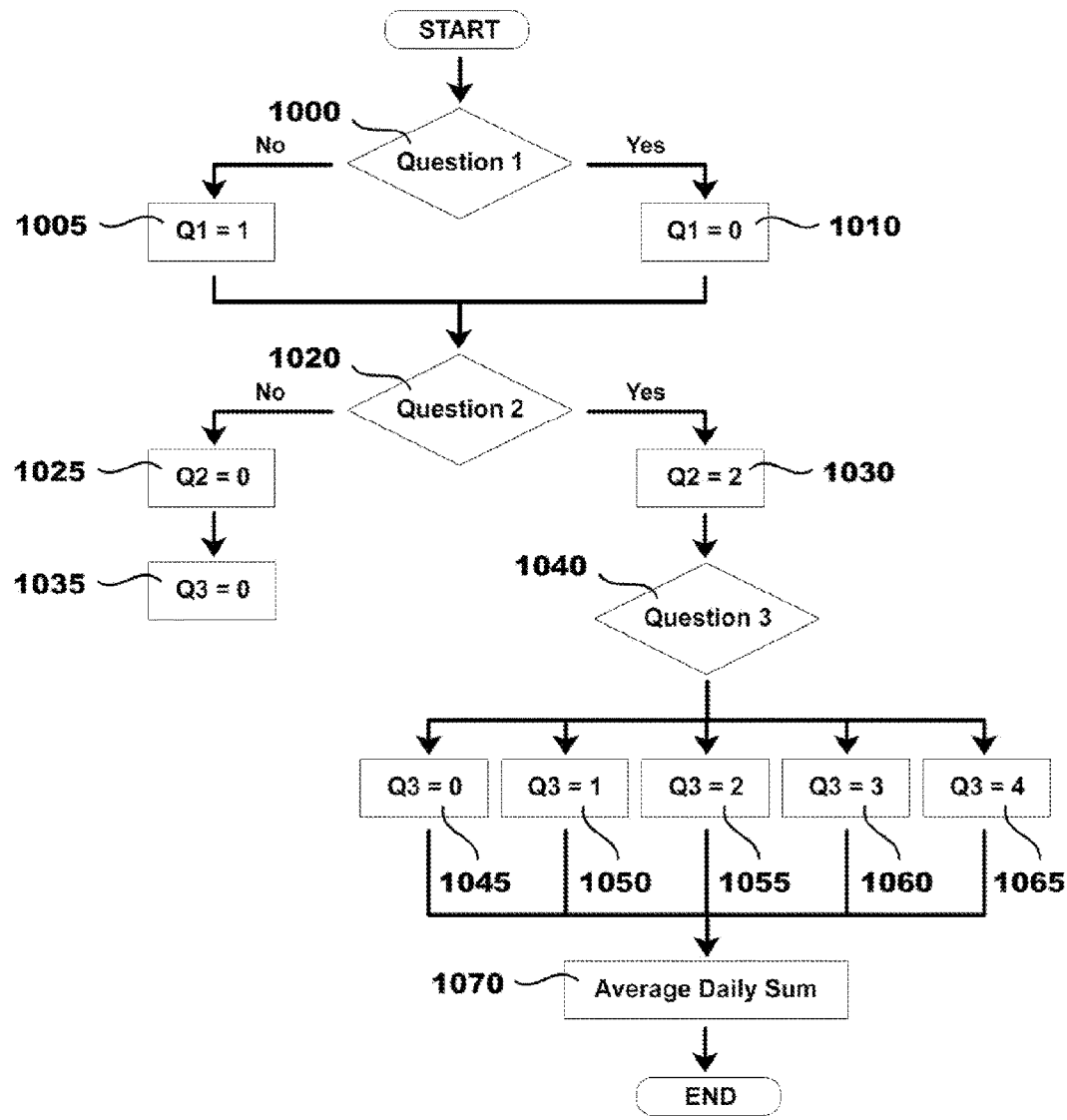
FIG. 10 illustrates another non-limiting example of a process flow for an algorithm for calculating a dysphagia symptom score.

Referring to FIG. 10, in a particular embodiment, a first question is for determining whether the patient avoided solid food 1000. An answer option indicating that the patient did not avoid solid food is assigned the numeric element 0 (e.g., Q1=0) 1010. An answer option indicating that the patient did avoid solid food is assigned the numeric element 1 (e.g., Q1=1) 1005. A second question is for determining whether the patient had difficulty swallowing solid food 1020. An answer option indicating that the patient did not have difficulty swallowing solid food is assigned the numeric element 0 (e.g., Q2=0) 1025. An answer option indicating that the patient did have difficulty swallowing solid food is assigned the numeric element 1 (e.g., Q2=2) 1030. A third question for determining what action the patient took to correct or relieve difficulty swallowing food 1040. In this embodiment, display of a third question for determining what action the patient took to correct or relieve difficulty swallowing food 1040 is contingent on an affirmative answer to a second question for determining whether the patient had difficulty swallowing solid food 1020. Accordingly, in this embodiment, where a patient indicates that they did not have difficulty swallowing solid food, a third question for determining what action the patient took to correct or relieve difficulty swallowing food is automatically assigned the numeric element 0 (e.g., Q3=0) 1035. Answer options to a third question for determining what action the patient took to correct or relieve difficulty swallowing food 1040 are assigned numeric elements based on the severity of the action. In this embodiment, an answer option indicating that the patient did not have to take action is assigned the numeric element 0 (e.g., Q3=0) 1045. An answer option indicating that the patient had to drink liquid is assigned the numeric element 1 (e.g., Q3=1) 1050. An answer option indicating that the patient had to cough and/or gag is assigned the numeric element 2 (e.g., Q3=2) 1055. An answer option indicating that the patient had to vomit is assigned the numeric element 3 (e.g., Q3=3) 1060. An answer option indicating that the patient had to seek medical attention is assigned the numeric element 4 (e.g., Q3=4) 1065. A daily score in this case is Q1+Q2+Q3 870.

Figure 11:
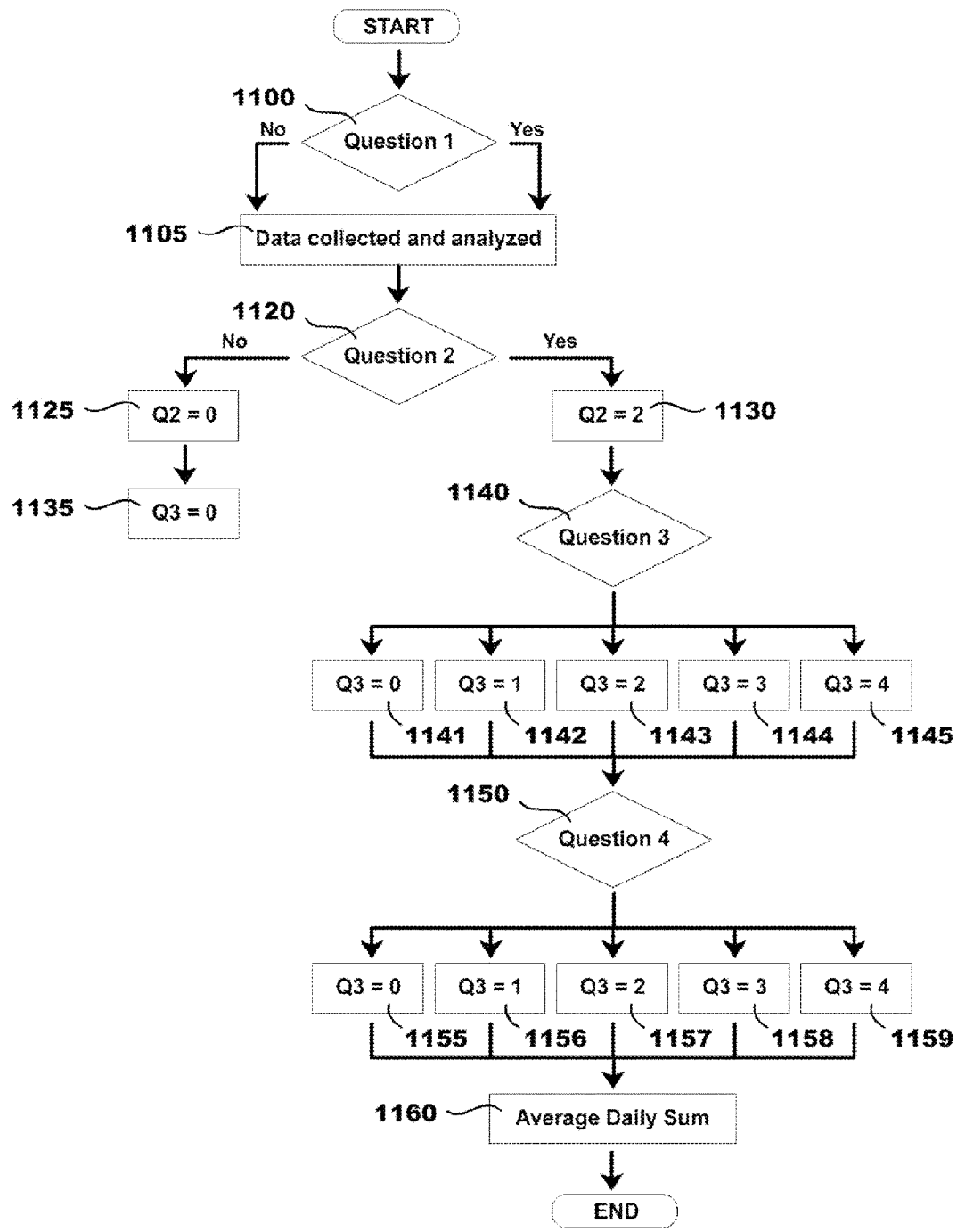
FIG. 11 illustrates another non-limiting example of a process flow for an algorithm for calculating a dysphagia symptom score.

Referring to FIG. 11, in a particular embodiment, a first question is for determining whether the patient avoided solid food 1100. Answer options indicating whether or not the patient avoided solid food are collected and analyzed, but not assigned numeric elements 1105. A second question is for determining whether the patient had difficulty swallowing solid food 1120. An answer option indicating that the patient did not have difficulty swallowing solid food is assigned the numeric element 0 (e.g., Q2=0) 1125. An answer option indicating that the patient did have difficulty swallowing solid food is assigned the numeric element 1 (e.g., Q2=1) 1130. A third question for determining what action the patient took to correct or relieve difficulty swallowing food 1140. In this embodiment, display of a third question for determining what action the patient took to correct or relieve difficulty swallowing food 1140 is contingent on an affirmative answer to a second question for determining whether the patient had difficulty swallowing solid food 1120. Accordingly, in this embodiment, where a patient indicates that they did not have difficulty swallowing solid food, a third question for determining what action the patient took to correct or relieve difficulty swallowing food is automatically assigned the numeric element 0 (e.g., Q3=0) 1135. Answer options to a third question for determining what action the patient took to correct or relieve difficulty swallowing food 1140 are assigned numeric elements based on the severity of the action. In this embodiment, an answer option indicating that the patient did not have to take action is assigned the numeric element 0 (e.g., Q3=0) 1141. An answer option indicating that the patient had to drink liquid is assigned the numeric element 1 (e.g., Q3=1) 1142. An answer option indicating that the patient had to cough and/or gag is assigned the numeric element 2 (e.g., Q3=2) 1143. An answer option indicating that the patient had to vomit is assigned the numeric element 3 (e.g., Q3=3) 1144. An answer option indicating that the patient had to seek medical attention is assigned the numeric element 4 (e.g., Q3=4) 1145. A fourth question for determining the amount of pain a patient experienced when swallowing food 1150. Answer options to a fourth question for determining the amount of pain a patient experienced when swallowing food 1150 are based on the severity of the pain. In this embodiment, an answer option indicating that the patient experienced no pain when swallowing food is assigned the numeric element 0 (e.g., Q4=0) 1155. An answer option indicating that the patient experienced mild pain when swallowing food is assigned the numeric element 1 (e.g., Q4=1) 1156. An answer option indicating that the patient experienced moderate pain when swallowing food is assigned the numeric element 2 (e.g., Q4=2) 1157. An answer option indicating that the patient experienced severe pain when swallowing food is assigned the numeric element 3 (e.g., Q4=3) 1158. An answer option indicating that the patient experienced very severe pain when swallowing food is assigned the numeric element 4 (e.g., Q4=4) 1159. A daily score in this case is Q2+Q3+Q4 1160.

In some embodiments, an algorithm described herein is optionally corrected for variations in patient compliance. In further embodiments, an algorithm detects and corrects for failure of a patient to complete a daily patient questionnaire. In still further embodiments, an algorithm described herein includes a question for determining whether the patient made efforts to avoid solid food during the course of a particular day. In some embodiments, a question for determining whether the patient avoided solid food is useful for discerning patient avoidance of food from absence of dysphagia symptoms. In some embodiments, an algorithm described herein is used to determine dysphagia-free days in any given time interval, which functions as an inherent correction for patient compliance.

In some embodiments, a score is a daily average score (e.g., sum of daily scores divided by number of days). Daily scores are suitably averaged over a wide range of time periods. In various embodiments, daily scores are averaged over 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days. In other various embodiments, daily scores are averaged over 1, 2, 3, 4, 5, 6, 7, 8, 9, 10, 11, 12, 13, 14, 15, 16, 17, 18, 19, 20, 21, 22, 23, 24 or more weeks. In other various embodiments, daily scores are averaged over 1, 2, 3, 4, 5, 6, 7, 8, 9, 10, 11, 12, 13, 14, 15, 16, 17, 18, 19, 20, 21, 22, 23, 24 or more months. In other various embodiments, daily scores are averaged over 1, 2, 3, 4, 5, 6, 7, 8, 9, 10 or more years.

The algorithm described herein is suitably tuned, in various embodiments, to focus on dysphagia symptom severity or detecting differences or changes in dysphagia symptom severity. In further embodiments, an algorithm described herein is optionally tuned to focus on dysphagia symptom severity by assigning higher numeric elements to answer options associated with a question for determining what action the patient took to correct or relieve difficulty swallowing food. For example, referring again to FIGS. 8 and 9, answer options associated with a question for determining what action the patient took to correct or relieve difficulty swallowing food are assigned numeric elements, 2, 4, 6, 8, and 10 or 3, 6, 9, 12, and 15 (rather than 1, 2, 3, 4, and 5). In such embodiments, symptom severity has a larger effect on the daily score and averaged daily scores.

The algorithm described herein is suitably tuned, in various embodiments, to focus on dysphagia symptom frequency or detecting differences or changes in dysphagia symptom frequency. In further embodiments, an algorithm described herein is optionally tuned to focus on dysphagia symptom frequency by assigning increased numeric elements to the answer options indicating the presence of dysphagia, where a patient selects such answer options in consecutive days. For example, referring again to FIGS. 8 and 9, an affirmative answer option associated with a question for determining whether the patient had difficulty swallowing solid food is assigned the numeric element 2 (rather than 1) on a second consecutive day, 3 (rather than 1) on a third consecutive day, and 4 (rather than 1) on a fourth consecutive day. In such embodiments, symptom frequency has a larger effect on the daily score and averaged daily scores.

A dysphagia symptom score or average daily score described herein has a wide range of suitable uses. In some embodiments, a dysphagia symptom score or average daily score is used in diagnosis. In some embodiments, diagnosis is the identification of the presence, nature, and/or cause of one or more symptoms, conditions, diseases, disorders, and/or injuries. In some embodiments, a dysphagia symptom score or average daily score is used illustrate, assess, or determine the determine presence of a condition, disorder, disease and/or injury. In some embodiments, a dysphagia symptom score or average daily score is used illustrate, assess, or determine the suitability of a patient for a particular diagnostic tool or diagnostic method. In some embodiments, a dysphagia symptom score or average daily score is used to illustrate, assess, or determine the suitability of a patient for a clinical trial for a particular diagnostic tool or diagnostic method. In some embodiments, a dysphagia symptom score or average daily score is used to illustrate, assess, or determine a patient's compliance with procedures, protocols, and/or regimens a clinical trial for a particular diagnostic tool or diagnostic method.

In some embodiments, a dysphagia symptom score or average daily score is used in diagnosis of dysphagia, symptoms of dysphagia, or a condition associated with dysphagia. In further embodiments, a dysphagia symptom score or average daily score is used in diagnosis of dysphagia associated with eosinophilic esophagitis or symptoms of dysphagia associated with eosinophilic esophagitis. In some embodiments, a score is used to, for example, access the suitability of a patient for a particular diagnostic tool or diagnostic method for dysphagia. In some embodiments, a score is used to, for example, access the suitability of a patient for inclusion in a clinical trial for a particular diagnostic tool or diagnostic method for dysphagia. In some embodiments, a score is used to, for example, access the compliance of a patient in a clinical trial for a particular diagnostic tool or diagnostic method for dysphagia.

In some embodiments, a dysphagia symptom score or average daily score is used in therapy (e.g., a treatment). In some embodiments, a therapy is any method of combating, ameliorating, or preventing one or more conditions, diseases, disorders, injuries, or one or more symptoms of the same. In various embodiments, a therapy is curative, palliative, prophylactic, a combination thereof. In various embodiments, therapy is behavioral, herbal, pharmacologic, immunologic, surgical, mechanical, supportive, or a combination thereof. In some embodiments, a dysphagia symptom score or average daily score is used illustrate, assess, or determine the suitability of a patient for a particular therapy. In further embodiments, a dysphagia symptom score or average daily score above a threshold value indicates suitability of a patient for a particular therapy. In other embodiments, a dysphagia symptom score or average daily score below a threshold value indicates suitability of a patient for a particular therapy. In some embodiments, a dysphagia symptom score or average daily score is used illustrate, assess, or determine the efficacy of a particular therapy. In further embodiments, a dysphagia symptom score or average daily score reduced below a threshold value indicates efficacy of a particular therapy. In other embodiments, a dysphagia symptom score or average daily score reduced by a threshold amount or percentage indicates efficacy of a particular therapy. In some embodiments, a dysphagia symptom score or average daily score is used illustrate, assess, or determine the suitability of a patient for a clinical trial for a particular therapy. In further embodiments, a dysphagia symptom score or average daily score above a threshold value indicates suitability of a patient for a particular clinical trial for a particular therapy. In other embodiments, a dysphagia symptom score or average daily score below a threshold value indicates suitability of a patient for a particular clinical trial for a particular therapy. In some embodiments, a dysphagia symptom score or average daily score is used illustrate, assess, or determine the compliance of a patient in a clinical trial for a particular therapy.

In some embodiments, a dysphagia symptom score or average daily score is used in therapy (e.g., treatment) for dysphagia, symptoms of dysphagia, or a condition associated with dysphagia. In further embodiments, a dysphagia symptom score or average daily score is used in therapy (e.g., treatment) for dysphagia associated with eosinophilic esophagitis or symptoms of dysphagia associated with eosinophilic esophagitis. In some embodiments, a score is used to, for example, assess suitability of a patient for a therapy for dysphagia, one or more symptoms of dysphagia, or a condition associated with dysphagia. In some embodiments, a score is used to, for example, assess efficacy of a therapy for dysphagia, one or more symptoms of dysphagia, or a condition associated with dysphagia. In some embodiments, a score is used to, for example, assess suitability of a patient for inclusion in a clinical trial for a diagnostic tool, a diagnostic method, or a therapy for dysphagia, one or more symptoms of dysphagia, or a condition associated with dysphagia. In some embodiments, a score is used to, for example, assess compliance of a patient in a clinical trial for a diagnostic tool, a diagnostic method, or a therapy for dysphagia, one or more symptoms of dysphagia, or a condition associated with dysphagia.

In some embodiments, the therapy comprises behavior modification. In some embodiments, the therapy comprises dietary intervention. In some embodiments, the therapy comprises pharmacologic therapy. In further embodiments, pharmacologic therapy involves one pharmacologic agent. In other embodiments, pharmacologic therapy involves a plurality of pharmacologic agents. In various embodiments, pharmacologic therapy involves 2, 3, 4, 5, 6, 7, 8, 9, 10 or more pharmacologic agents. In some embodiments, the therapy comprises immunotherapy. In further embodiments, immunotherapy involves one or more modulators, inducers, enhancers, or suppressors of the immune system. In still further embodiments, immunotherapy involves one or more recombinant, synthetic and/or natural cytokines, chemokines, cells, and/or antibodies. In some embodiments, the therapy comprises combination of therapies (e.g., treatments) and/or types of therapies.

In some embodiments, the therapy comprises orally administering to the patient an effective amount of a proton pump inhibitor (PPI), e.g., omeprazole, lansoprazole, dexlansoprazole, esomeprazole, pantoprazole, or rabeprozole.

In some embodiments, the therapy comprises orally administering to the patient an effective amount of a corticosteroid. Typically, the corticosteroid is a topically active corticosteroid. Suitable corticosteroids include, but are not limited to, aclometasone, amcinomide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fuprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, remexolone, tixocortol, triamcinolone, ulobetasol, or a pharmaceutically acceptable salt or ester thereof, or a combination thereof. In some embodiments, the corticosteroid is budesonide, fluticasone, mometasone, desonide, ciclesonide, triamcinolone, beclomethasone, or a pharmaceutically acceptable ester thereof, or a combination thereof.

In some embodiments, the corticosteroid is budesonide. In further embodiments, budesonide is administered orally. In still further embodiments, budesonide is administered as an oral liquid suspension.

In some embodiments, the therapy comprises mechanical intervention. In further embodiments, the therapy comprises mechanical dilation of the esophagus. In some embodiments, a score disclosed herein is used to, for example, assess the suitability of mechanical therapy, such as esophageal dilation, for a particular patient. In some embodiments, a score disclosed herein is used to, for example, assess efficacy of mechanical therapy, such as esophageal dilation, for a particular patient. In some embodiments, a score disclosed herein is used to, for example, assess a suitable time interval to repeat a mechanical therapy, such as esophageal dilation, for a particular patient.

In some embodiments, a score described herein illustrates reduction in esophageal inflammation and symptoms of dysphagia in patients with eosinophilic esophagitis.

In various embodiments, a dysphagia symptom score or average daily score described herein is useful for assessing, by way of non-limiting embodiments, severity, intensity, or frequency of patient dysphagia; severity, intensity, or frequency of one or more patient symptoms of dysphagia; suitability of a patient for a particular diagnostic tool, diagnostic method, or therapy for dysphagia; suitability of a patient for a particular diagnostic tool, diagnostic method, or therapy for one or more symptoms of dysphagia; efficacy of a particular therapy for dysphagia; efficacy of a particular therapy for one or more symptoms of dysphagia; suitability of a patient for a clinical trial; and compliance of a patient in a clinical trial.

In various further embodiments, a dysphagia symptom score or average daily score described herein is useful for assessing, by way of non-limiting embodiments, severity, intensity, or frequency of patient dysphagia associated with eosinophilic esophagitis; severity, intensity, or frequency of one or more patient symptoms of dysphagia associated with eosinophilic esophagitis; suitability of a patient for a particular diagnostic tool, diagnostic method, or therapy for dysphagia associated with eosinophilic esophagitis; suitability of a patient for a particular diagnostic tool, diagnostic method, or therapy for one or more symptoms of dysphagia associated with eosinophilic esophagitis; efficacy of a particular therapy for dysphagia associated with eosinophilic esophagitis; efficacy of a particular therapy for one or more symptoms of dysphagia associated with eosinophilic esophagitis; suitability of a patient for a clinical trial; and compliance of a patient in a clinical trial.

Transmission

In some embodiments, a daily patient reporting tool further comprises a software module configured to communicate (e.g., transmit, etc.) patient answers to a centralized server, database, or portal. In further embodiments a software module configured to communicate patient answers to a centralized database communicates information to a centralized server, database, or portal for processing (e.g., application of an algorithm, etc.), storage, or display (e.g., to a patient, a caregiver, or a healthcare provider, etc.). In some embodiments, a software module configured to communicate patient answers also communicates other patient information such as that pertaining to patient compliance with the questionnaire and daily diary regimen. In some embodiments, a software module configured to communicate patient answers to a centralized server, database, or portal satisfies the privacy and security requirements of the Health Insurance Portability and Accountability Act of 1996 (HIPAA).

Many transmission protocols are suitable. In some embodiments, a software module configured to communicate patient answers to a centralized server, database, or portal utilizes Transmission Control Protocol/Internet Protocol (TCP/IP), including for example, Hypertext Transfer Protocol (HTTP), Simple Mail Transfer Protocol (SMTP), File Transfer Protocol (FTP), Secure Shell (SSH), Post Office Protocol (POP), and Internet Message Access Protocol (IMAP), and combinations thereof to transmit information. In some embodiments a software module configured to communicate patient answers to a centralized server, database, or portal utilizes, by way of non-limiting examples, Short Message Service (SMS), Multimedia Message Service (MMS), web-based email, instant messaging, and combinations thereof to transmit information. In some embodiments, a software module configured to communicate patient answers to a centralized server, database, or portal utilizes, by way of non-limiting examples, Wi-Fi, 3G (3rd generation mobile telecommunications), 4G (4th generation mobile telecommunications), and geosynchronous and low Earth orbit (LEO) satellite, and combinations thereof to transmit information. In other embodiments, a software module configured to communicate patient answers to a centralized server, database, or portal utilizes short-range wireless protocols, by way of non-limiting examples, Bluetooth, ZigBee, and combinations thereof to transmit information.

Notification

In some embodiments, a daily patient reporting tool further comprises a software module configured to provide a notification or reminder to a patient to complete a daily patient questionnaire. In further embodiments, a software module configured to provide a notification or reminder to a patient improves the accuracy and reliability of the questionnaire by encouraging a patient to provide complete information and to provide the information during a short recall period while the information is recent. In some embodiments a software module configured to provide a notification or reminder to a patient to complete a daily patient questionnaire satisfies the privacy and security requirements of the Health Insurance Portability and Accountability Act of 1996 (HIPAA).

In some embodiments, the function of a software module configured to provide a notification or reminder to a patient is pre-configured in the daily patient reporting tool. In further embodiments, the software module provides a notification or reminder to a patient, if the questionnaire is not complete, at the end of each day. In still further embodiments, the software module provides a notification or reminder to a patient, if the questionnaire is not complete, for example, at the 6 PM, 7 PM, 8 PM, 9 PM, 10 PM or 11 PM, each day, including increments of time therein.

In some embodiments, if a notification or reminder does not stimulate a patient to complete the questionnaire, a follow-up notification or reminder is sent. In some embodiments, a follow-up notification or reminder is sent to the patient. In other embodiments, a follow-up notification or reminder is sent to a family member, friend, or caregiver for the patient. In yet other embodiments, a follow-up notification or reminder is sent to a healthcare provider for the patient.

In some embodiments, a notification or reminder is an alarm or alert utilizing audio and visual output capacity of a digital processing device (e.g., desktop computer, laptop computer, tablet computer, mobile device, smartphone, etc.). In other embodiments, a notification or reminder is, by way of non-limiting examples, an email, SMS, MMS, automated phone call, voice mail, blog post, microblog post, social network post, instant message, or combination thereof.

In some embodiments, the function of a software module configured to provide a notification or reminder to a patient is configured by a patient. In further embodiments, a patient configures, by way of non-limiting examples, notification time, alarm volume, alarm sound effect, notification message, notification medium (e.g., plain text, HTML, RTF, graphic, etc.), notification channel (e.g., SMS, email, IM, etc.), recipient for follow-up notifications, and the like.

Non-transitory Computer Readable Storage Medium

In some embodiments, the methods, systems, and software disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the methods, systems, and software disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBeny® SDK, BREW SDK, Palm° OS SDK, Symbian SDK, webOS SDK, and Windows° Mobile SDK.

Those of skill in the art will recognize that several commercial forums are available for distribution of mobile applications including, by way of non-limiting examples, Apple° App Store, Android™ Market, BlackBerry® App World, App Store for Palm devices, App Catalog for webOS, Windows° Marketplace for Mobile, Ovi Store for Nokia° devices, Samsung° Apps, and Nintendo° DSi Shop.

Software Modules

In some embodiments, the methods, systems, and software disclosed herein include software, server, and database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

EXAMPLES

Example 1

Field Trial of an Electronic Dysphagia Symptom Questionnaire (DSQ) with EoE Patients Materials and Methods Twenty patients participated in Cognitive Interviews (CIs) at the start of the field trial. Thirty-seven patients (18 adolescents and 19 adults) from four recruitment sites participated in the study. Patients had to have a histologic diagnosis of EoE, have persistent dysphagia, and agree to use an electronic DSQ for at least 30 days.

A paper-based 3-item DSQ (see FIG. 12) was converted into an electronic format for hand-held devices by PHT (PHT Corporation, 500 Rutherford Avenue, Charlestown, Mass. 02129). In this case, the items are text-based questions and the DSQ is a 3-question instrument. However, many items are suitable for eliciting appropriate input from patients including, by way of non-limiting examples, text-based questions, audio questions, video questions, and graphical questions (e.g., pictograms, etc.). These devices were programmed to sound an alarm at the end of the day (time selected by patient) to remind patients to complete their daily diaries. All field trial participants visited a recruitment site to obtain the device and receive training on its use. Participants were instructed to answer questions about the frequency and intensity of their symptoms on the daily diary for a 30-day period. The start date of the field trial was the date that patient data was first sent from the device. Patients from two sites were asked to complete the Straumann Weekly Dysphagia Score during their last visit. This dysphagia instrument was adapted from the literature and administered in the form of a questionnaire with a one-week look back period. See Straumann A, et al. Budesonide is Effective in Adolescent and Adult Patients with Active Eosinophilic Esophagitis. *Gastroenterology*. 2010; 139: 1526-1537.

The following parameters were evaluated over the 30 day course of the study for the overall population. Some parameters were also evaluated by age category, topical steroid usage, and other therapy:

Compliance: Number of responded days and percentage of responded days.
Solid food avoidance: Number of solid-food avoidance days and percentage of solid food avoidance days.
Difficulty swallowing (dysphagia): Number of dysphagia days and percentage of dysphagia days.
Action taken to get relief: Any "Yes" response to DSQ item 2 led to categorical scoring of action taken in item 3. Responses were summarized using descriptive statistics.

An algorithm was proposed to calculate dysphagia scores. Scores were computed for 4 weekly intervals based on the number of dysphagia days per week. Additional analyses included pattern of response to items tabulated in weekly (7 day) increments.

Lastly, cognitive interview data were coded and compared. The analyzed concepts focused on patient interpretation of items, patient suggestions regarding rewording or deletion of items, patient reports regarding relevance of items, and other concepts focusing on the electronic DSQ instead of the physical symptoms of EoE and their impact. Responses to the questions in the semi-structured cognitive interviews were evaluated to determine whether the instrument met the following conditions:

Required purpose of the final instrument;
Qualitative agreement with input from patients with EoE;
Agreement with the output of an importance-ranking exercise with EoE patients; and
Ability to support a labeling claim for the symptom component of a compound primary endpoint.

Results

Demographic and EoE Treatment Information

Summary demographic and EoE treatment information is provided in Table 2. Eighteen adolescents aged 12-17 years and 19 adults aged 18-45 years participated in the field trial. The majority of the subjects were Caucasian and approximately 54% of subjects were male. While this study was non-interventional, current EoE treatments were recorded for participants. Thirteen adolescents (72.2%) were treated with topical steroids including swallowed Flovent and makeshift oral budesonide slurries whereas only seven (36.8%) adults were being treated with topical steroids.

TABLE 2

Summary Demographics and EoE Treatment Information for Field Trial Participants

| | Adolescents (N = 18) n (%) | Adults (N = 19) n (%) | Total (N = 37) n (%) |
|---|---|---|---|
| Gender | | | |
| Male | 11 (61.1%) | 9 (47.4%) | 20 (54.1%) |
| Female | 7 (38.9%) | 10 (52.6%) | 17 (45.9%) |
| Age | | | |
| Range | 12-17 | 18-45 | 12-45 |
| Mean (SD) | 15.2 (1.6) | 31.7 (9.3) | 23.6 (10.7) |
| Race | | | |
| Black or African American | 1 (5.6%) | 0 (0.0%) | 1 (2.7%) |
| White/Caucasian | 16 (88.9%) | 19 (100.0%) | 35 (94.6%) |
| Other | 1 (5.6%) | 0 (0.0%) | 1 (2.7%) |
| EoE Treatments During Course of Field Trial | | | |
| Topical Steroid | 13 (72.2%) | 7 (36.8%) | 20 (54.1%) |
| Other Treatments Including Proton Pump Inhibitor, Dietary Therapy or No Treatment | 5 (27.8%) | 12 (63.2%) | 17 (45.9%) |

Figure 13:
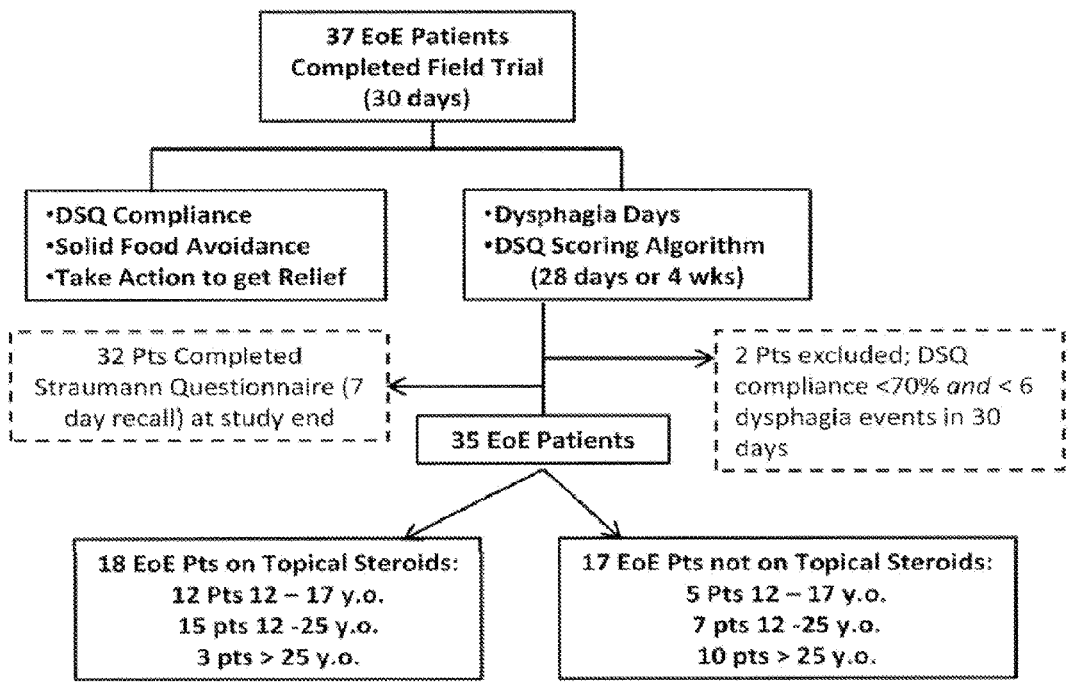
FIG. 13 depicts the disposition of field trial patients and analysis of field trial data.

Data were collected for the 37 patients over the 30 day study period. FIG. 13 shows the data sub-sets used to analyze the various DSQ components. Patient compliance in use of the DSQ, solid food avoidance, and actions to get relief are reported below for all 37 subjects for the 30 day period. The dysphagia days and DSQ score were analyzed for the first 28 days of data collection, divided in 4 weekly segments. Two patients were excluded from this analysis because their compliance with the program was <70% and they individually reported fewer than 6 dysphagia events in 30 days. Dysphagia days and corresponding DSQ scores were analyzed for the remaining 35 patients, of whom 18 were being treated with topical steroids and 17 were being treated with other or no therapy. During their last study visit, 32 subjects completed the Straumann weekly Dysphagia Score.

Compliance

DSQ compliance, measured by response to at least one DSQ item, was high and similar between adolescent and adult patients (86.7% and 83.3% respectively).

Solid Food Avoidance

A "No" answer to question 1 (Since you woke up this morning, did you eat solid food?) signified solid food avoidance. Nine patients indicated they had not eaten solid food on at least one of the reported days, with maximum avoidance being 15 days for one adult patient and 6 days for one adolescent patient.

Dysphagia Days

Figure 14:
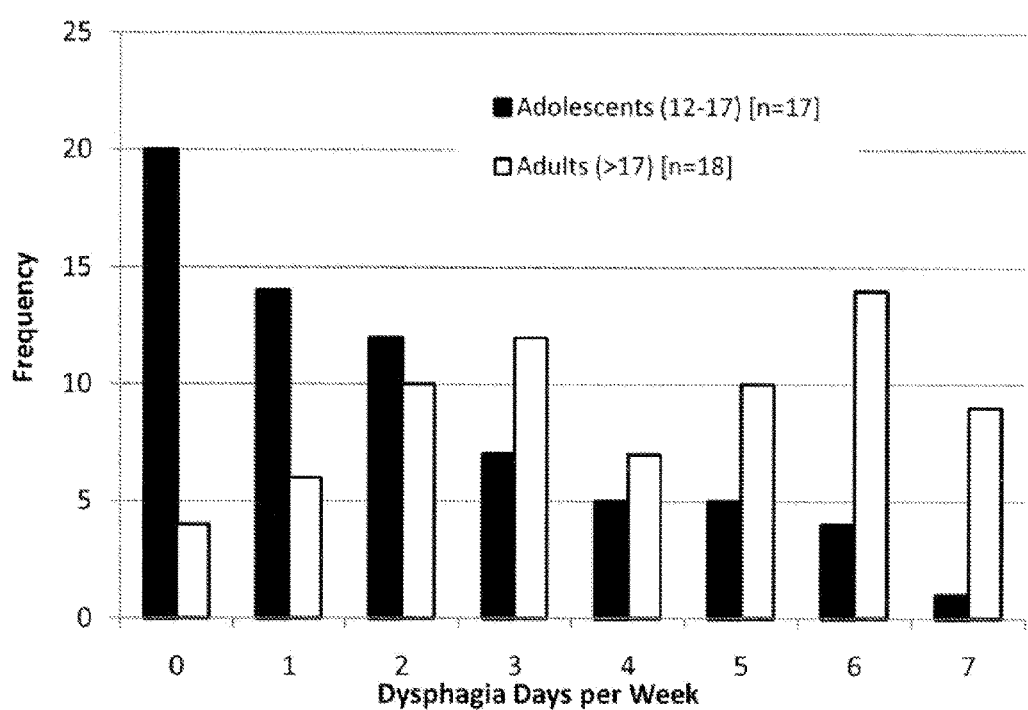
FIG. 14 depicts data from the field trial of Example 1; specifically, frequency (count) of dysphagia days per week for adolescent and adult EoE patients reported over 4 weeks.
Figure 15:
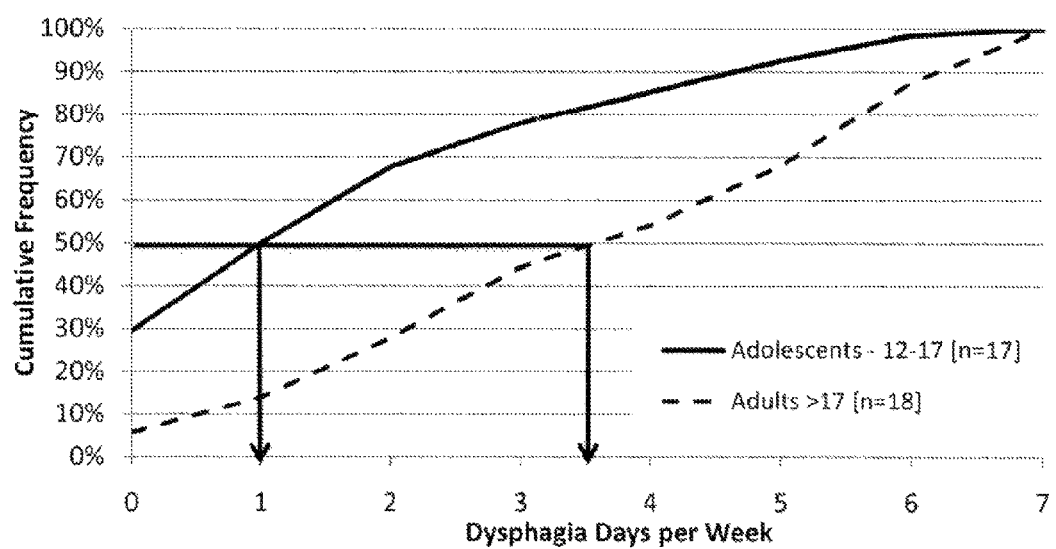
FIG. 15 depicts data from the field trial of Example 1; specifically, cumulative frequency of dysphagia days per week for adolescents and adults.

DSQ item 2 (Since you woke up this morning, has food gone down slowly or been stuck?) measured the frequency of dysphagia on a daily basis. The number of dysphagia days reported per week was counted for each of the 4 weeks for 35 patients. FIG. 14 plots dysphagia days per week versus the frequency (count) for adolescent (solid bar) and adult (open bar) subjects. The peak number of dysphagia days per week was 1 and 6 for adolescents 12-17 years of age and adults, respectively. The data in FIG. 14 were re-plotted in FIG. 15 as a cumulative distribution for adolescents (solid line) and adults (dashed line).

The median number (50% line FIG. 15) of dysphagia days per week was approximately 1 for adolescents and 3-4 for adults. These data suggest that the DSQ is able to measure dysphagia events across the adolescent and adult patient population. It is not clear whether the lower number of dysphagia days in adolescents is related to the nature of EoE disease or its treatment. As shown in Table 2, more adolescents than adults in this study were being treated with topical steroids.

Figure 16:
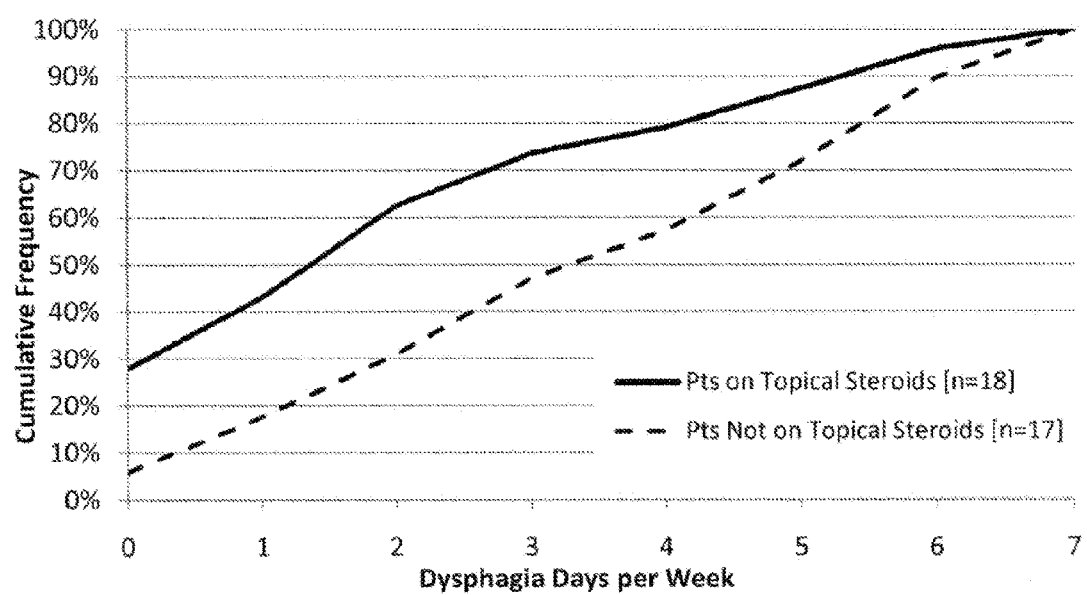
FIG. 16 depicts data from the field trial of Example 1; specifically, cumulative frequency of dysphagia days per week for patients with and without topical steroid treatment.

In FIG. 16, the number of dysphagia days reported per week versus the cumulative frequency for the 4 weeks is shown for EoE patients being treated with topical steroids (n=18, solid line) versus those receiving other treatments (i.e., PPIs, diet) or no therapy (n=17, dashed line).

The median number of dysphagia days for topical-steroid treated patients (approximately 1-2 per week) is clearly less than that for those patients not on steroid therapy (3 days per week). This suggests that the DSQ is able to detect differences in dysphagia frequency between treatment groups.

Figure 17:
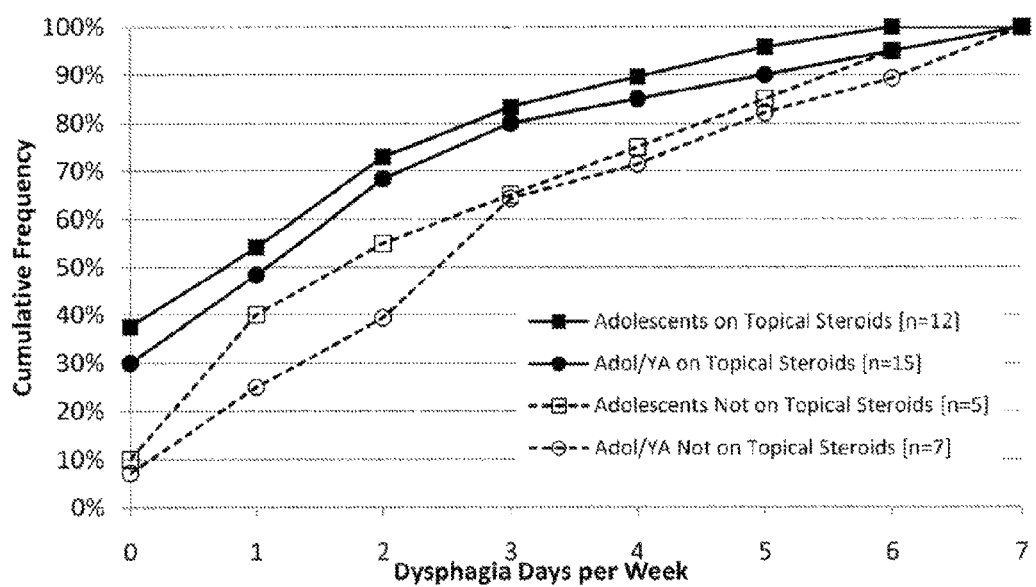
FIG. 17 depicts data from the field trial of Example 1; specifically, dysphagia days per week for adolescents (12-17 years) versus adolescents and young adults (12-25 years), with and without topical steroid treatment.

In FIG. 17, the number of dysphagia days reported per week is plotted against the cumulative frequency over 4 weeks for the adolescent population (12-17 years of age; square symbols) and an expanded adolescent population that includes young adults up to 25 years of age (round symbols). The data for patients with (solid lines) and without (dashed lines) topical steroid treatment is shown for both populations. These data show that dysphagia episodes occur with similar frequency in the adolescent population and the expanded adolescent/young adult populations, but as in FIG. 16, it appears that patients treated with topical steroids have fewer dysphagia episodes per week.

Symptom Response/Action to Get Relief

Item 3 of the DSQ asked "For the most difficult time you had swallowing today, did you have to do anything to make the food go down or get relief?" Five response options were provided, ranging from no action to seeking medical attention. Table 3 below summarizes the number of days in the field trial that an action was taken by patients in response to symptoms. Because subjects only move to Item 3 after they had positively indicated in Item 2 that food had gone down slowly or been stuck, the number of symptom days is also shown in Table 3.

TABLE 3

Field Trial Results: Response to Symptoms/Days Patients Took Action to Get Relief When Symptoms Were Present

| | | Item 3 | | | | |
|---|---|---|---|---|---|---|
| | Item 2 Dysphagia Days | No action | Drink Liquid | Cough and/or Vomit | Vomit | Seek Medical Attention |
| | | | Dysphagia Days with Action to Get Relief | | | |
| Adolescents | | | | | | |
| Mean (SD) | 8.1 (6.8) | 4.1 (3.3) | 3.9 (4.2) | 0.8 (1.4) | 0.2 (0.5) | 0 (0.0) |
| Median | 8.0 | 3.5 | 2.0 | 0.0 | 0 | 0 |
| Range | 0-22 | 0-10 | 0-11 | 0-4 | 0-2 | 0 |
| Adults | | | | | | |
| Mean (SD) | 16.8 (8.1) | 4.3 (5.3) | 9.0 (8.8) | 2.8 (4.2) | 0.5 (1.1) | 0.2 (0.7) |
| Median | 19 | 2.0 | 9.0 | 2.0 | 0 | 0 |
| Range | 4-29 | 0-17 | 0-26 | 0-16 | 0-4 | 0-3 |

Adolescents reported fewer dysphagia days than adults and when the dysphagia symptoms occurred adolescents took no action to get relief about half the time (approximately 4 of 8 days). Adults took action on approximately 12 of the 17 symptom days. It is not clear whether this difference reflects a difference in disease state or a difference in background treatment. The majority of adolescent patients were being treated with topical steroids (see Table 2). Both adolescent and adult data suggest that the response categories were correctly ordered with responses less frequent as the intensity of response increased.

Final DSQ Content and Proposed Scoring Algorithm

Cognitive interviews were conducted with 20 EoE patients at the start of the field trial to evaluate the face and content validity of the DSQ. Nineteen of these patients (10 adolescents and 9 adults) went on to participate in the field trial. During the CIs, most patients reported that the DSQ was easy to understand and relevant to their condition. In addition, most of the patients gave positive feedback on the electronic format of the DSQ and indicated it would be easy to complete over two weeks or one month.

The proposed algorithm can be considered as follows:
If Q1="No" then score Q1=1 else if Q1="Yes" then Q1=0
If Q2="Yes" then score Q2=1 else if Q2="No" then Q2=0
If Q2="No" then Q3=0
If Q2=1 then score Q3 rating scale as 1 to 5 (depending on response choice)
Week 1_Score=Sum Days 1-7 divided by N of Days 1-7
Week2_Score=Sum Days 8-14 divided by N of Days 8-14
The DSQ score can be determined over one week or multiple weeks, with the denominator, N, as the number of reported days. Thus, a 2-week or 4-week DSQ score would be no greater than a one-week DSQ score, as the denominator would increase. For clinical trial use, the two-week score, should effectively minimize variability in the daily symptoms which is characteristic of EOE, while being sensitive to change in the therapeutic regimen.

The proposed algorithm was applied to the data presented in FIG. 17 and is shown in Table 4 below. Although the field trial was a non-interventional study of EoE patients and the sample sizes are small, the data in Table 4 data suggest that the DSQ may be able to discriminate between treatment groups.

TABLE 4

DSQ Scores By Week: Adolescent and Young Adult Patients With and Without Topical Steroid Treatment

| | DSQ Score (s.d.) Based on Proposed Algorithm | |
|---|---|---|
| | Patients (12-25) with topical steroids N = 15 | Patients (12-25) without topical steroids |
| Week 1 | 0.87 (0.86) | 1.89 (1.27) |
| Week 2 | 1.02 (1.02) | 1.79 (1.12) |
| Week 3 | 0.96 (0.90) | 1.92 (1.63) |
| Week 4 | 0.84 (0.97) | 2.14 (1.44) |

Figure 18:
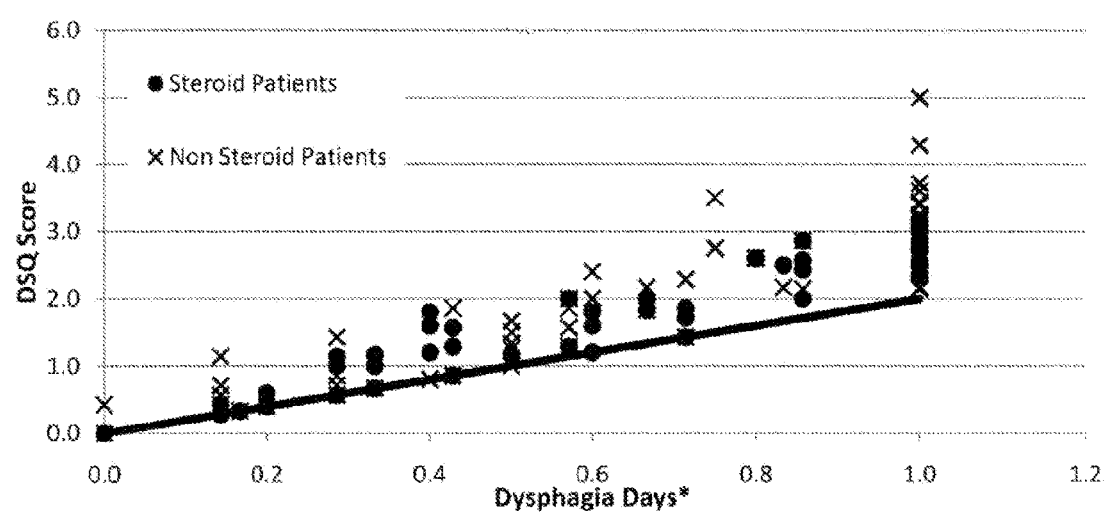
FIG. 18 depicts data from the field trial of Example 1; specifically, correlation between dysphagia days and dysphagia score based on the proposed scoring algorithm.

The proposed algorithm, measures both the frequency of dysphagia days and intensity of the worst episodes as reflected by the response to symptoms/action taken. The correlation of number of dysphagia days per week versus the DSQ score is shown in FIG. 18. The data suggest that increasing frequency of symptoms is associated with increasing intensity of symptoms as reflected by response to symptoms/action taken in the DSQ. The solid line in FIG. 18 has a slope of 2 reflecting the relationship between dysphagia days and score. Points above the line reflect the additional scoring components of food avoidance, action taken to get relief or both. As dysphagia days increase, the intensity of symptom response contributes more heavily to the DSQ score.

Correlation with Straumann Dysphagia Instrument

EoE-related dysphagia has been evaluated in earlier clinical trials using other outcome measures. As Straumann was successful in demonstrating response to oral budesonide using his physician-reported outcome measure, the performance of the DSQ was further evaluated by comparing it to the Straumann instrument in the field trial. During week 4 of the field trial, patients were asked to complete both the DSQ and a patient questionnaire derived from Straumann's physician-administered instrument.

Figure 19:
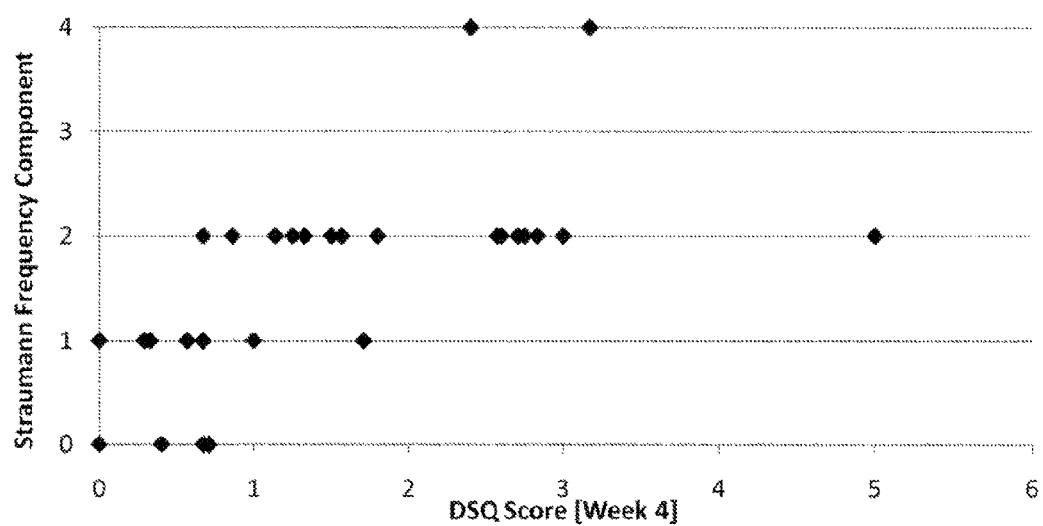
FIG. 19 depicts data from the field trial of Example 1; specifically, field trial correlation of dysphagia frequency (Straumann Dysphagia Questionnaire) with the electronic DSQ score for all subjects (n=32).

Week 4 data were available for a total of 32 subjects. Data from the two dysphagia instruments were correlated, using the frequency data from the Straumann instrument and the combined frequency/intensity data from the DSQ score. Because the ordering of the Straumann intensity items did not match the ordering of the DSQ intensity items, no attempt was made to correlate the intensity items directly. The Spearman correlation coefficient was determined, as both instruments collected frequency data using an ordered categorical (rather than continuous) scale. The results are shown in FIG. 19. As shown in FIG. 19, the dysphagia data collected with the DSQ and Straumann instruments correlate with a high degree of statistical significance (Spearman Correlation=0.77 ($p<0.001$)).

Discussion and Conclusions

The DSQ described herein captures information regarding the frequency and intensity/severity of dysphagia symptoms. Unlike previous instruments, the DSQ is an electronic application administered on a daily basis, assuring more accurate recall than is possible with a one or two week recall period. The score derived from the DSQ is driven primarily by the frequency of events (Item 2), but Item 3 queries patients about their response to symptoms, asking what action they have taken to achieve relief The categorical response options are arranged in hierarchical manner with "no action" and the least bothersome action (drinking liquids) receiving the least weight, and the most bothersome actions, vomiting and seeking medical attention (for removal of food impaction) receiving the most weight. Cognitive interviews with EoE patients confirmed that the hierarchy is correct and that the response options are viewed by patients as surrogates for the increasing intensity of the dysphagia symptoms themselves. This is supported by field trial data. When patients selected an option to describe the most bothersome dysphagia event of the day, the greater the intensity became, the less frequently that option was selected (see Table 3). Drinking liquids to get relief occurred on approximately half of the symptom days, while just 3 patients had to seek medical attention on one occasion to get relief Field trial data were consistent with good item separation in the Item 3 categorical scale.

The food avoidance question (Item 1) performed as intended. Patients who were experiencing frequent troublesome dysphagia symptoms avoided eating solid food on 32 occasions during the 30-day field trial. Although this behavior was generally accompanied by the absence of dysphagia symptoms on the avoidance day, the component of the score assigned to avoidance assured that absence of symptoms would not be recorded as improvement in the disease state.

Using the proposed DSQ scoring algorithm, the score can be determined over one week or multiple weeks, with the denominator as the number of reported days. Thus, a 2-week or 4-week DSQ score would be no greater than a one-week DSQ score, as the denominator would increase.

Several correlations indicated that the DSQ and the proposed DSQ scoring algorithm, were performing in a predictable and consistent manner. The DSQ score correlated well with dysphagia frequency, indicating that patients with increasing frequency of dysphagia episodes also experienced increasing intensity of symptoms. A correlation of the DSQ score with dysphagia frequency recorded by a modified Straumann questionnaire also showed a high degree of statistical significance.

The data in Table 5 data indicate that dysphagia emerges with increasing age as the most severe, most bothersome, most frequent, and most important symptom in EoE patients as reported by patients and caregivers. Table 5 supports that dysphagia is the right symptom to measure in EoE patients 12 years old or older.

TABLE 5

Symptom Rankings by Patients And Caregivers in EoE: Emergence of Dysphagia with Increasing Age

| Symptom Category | 2-5 years* (n = 10) | 6-11 years (n = 10) | 12-18 years (n = 10) |
|---|---|---|---|
| Most severe | 1. Vomiting<br>2. Abdominal pain<br>3. Diarrhea<br>4. Odynophagia | 1. Dysphagia<br>2. Vomiting<br>3. Abdominal pain<br>4. Heartburn | 1. Dysphagia<br>2. Abdominal pain<br>3. Heartburn<br>4. Vomiting |
| Most bothersome | 1. Vomiting<br>2. Abdominal pain<br>3. Diarrhea<br>4. Odynophagia | 1. Abdominal pain<br>2. Heartburn<br>3. Dysphagia<br>4. Vomiting | 1. Dysphagia<br>2. Abdominal pain<br>3. Reflux<br>4. Chest Pain |
| Most frequent | 1. Cough/gag<br>2. Regurgitation<br>3. Vomiting<br>4. Dysphagia | 1. Abdominal pain<br>2. Heartburn<br>3. Dysphagia<br>4. Vomiting | 1. Dysphagia<br>2. Abdominal pain<br>3. Heartburn<br>4. Throat pain |
| Most important | 1. Vomiting<br>2. Cough/gag<br>3. Abdominal pain<br>4. Odynophagia | 1. Vomiting<br>2. Dysphagia<br>3. Abdominal pain<br>4. Odynophagia | 1. Dysphagia<br>2. Abdominal pain<br>3. Heartburn<br>4. Vomiting |

Symptom rankings determined during concept elicitation interviews conducted before the field trial
*Caregivers only Example 2

Clinical Study of an Oral Budesonide Solution in Adolescents and Adults with EoE Using an Electronic Dysphagia Symptom Questionnaire (DSQ)

Objective

To demonstrate that an oral budesonide solution (OBS) induces, over a 12-week course of therapy:
a histologic response in adolescent and adult subjects with EoE; and
a symptom response as measured by the Dysphagia Symptom Questionnaire (DSQ).

Design

A randomized, placebo-controlled, double-blind study with 2 arms was conducted at 25-30 EoE centers in US. The study included a 24 week open label extension (OLE). Patients were given a placebo for a 4-week period to establish a Baseline for the co-primary endpoint determinations. Patients were then divided into 2 groups, one receiving OBS treatment and the other continued placebo for a 12-week period. Patients in the OLE were given OBS once daily for 24 weeks following a Final Treatment Period Evaluation at week 16.

Treatments and Dose

Oral budesonide suspension (0.2 mg/mL) and matched placebo; 10 mL/dose, given twice daily in Treatment Period and once-daily in OLE.

Subjects 93 randomized EoE subjects 11-40 years old with >15/HPF at two levels of the esophagus and persistent dysphagia after 4 week blinded placebo Baseline period.

Co-Primary Endpoints

The two co-primary endpoints were the change in the DSQ score from Baseline to the Final Treatment Period Evaluation, and the proportion of subjects who were histologic responders. For each subject, histologic response was defined as a peak eosinophil count of <6/HPF across all available esophageal levels at the Final Treatment Period Evaluation.

Other Parameters

Safety for dosing up to 36 consecutive weeks.

Statistical Methods

Definition of Analysis Sets

Safety analysis set includes all subjects who received at least one dose of double blind study medication. Subjects are analyzed based on actual treatment received.

Modified Intent-to-Treat (MITT) analysis set includes all randomized subjects who received at least one dose of double blind study drug and have both an evaluable post-baseline biopsy in the Treatment Period (i.e., peak eosinophil count was reported for at least two esophageal levels) and a post-baseline DSQ score. MITT analysis set was used for all efficacy analyses.

Per Protocol analysis set includes all subjects in the MITT analysis set who have had a final biopsy, at 12 weeks or earlier, and who, in the opinion of the Sponsor, have not deviated significantly from the protocol.

Randomization

Subjects were randomized at Baseline Visit 2 using a computer generated schedule. Randomization was stratified by site and subjects were randomly assigned in a 1:1 ratio.

Statistical Analysis and Data Presentation

The primary analysis set for each of the two co-primary endpoints was completed using the MITT analysis set that compared the OBS and placebo groups using a two-sided test at the 5% level of significance. The change from baseline DSQ Score at the Final Treatment Evaluation was analyzed using ANCOVA with treatment group as a factor and the baseline DSQ score as a covariate. The proportion of subjects who were histologic responders was compared using the Fisher's exact test. The proportion of subjects who were DSQ responders was compared using Pearson's chi squared test.

Results

The clinical study subject disposition is summarized in Table 6.

TABLE 6

Clinical Study Subject Disposition

| | Placebo | OBS 2 mg bid | All Subjects |
|---|---|---|---|
| Subjects Randomized | 42 | 51 | 93 |
| Safety Analysis Set | 42 (100.0%) | 51 (100.0%) | 93 (100.0%) |
| MITT Analysis Set | 38 (90.5%) | 49 (96.1%) | 87 (93.5%) |
| PP Analysis Set | 34 (81.0%) | 44 (86.3%) | 78 (83.9%) |
| Subjects Who Completed the Treatment Period | 39 (92.9%) | 49 (96.1%) | 88 (94.6%) |
| Subjects Who Discontinued During the Treatment Period | 3 (7.1%) | 2 (3.9%) | 5 (5.4%) |
| Primary Reason Subjects Did Not Complete the Treatment Period | | | |
| Adverse Event | 0 (0.0%) | 1 (2.0%) | 1 (1.1%) |
| Significant Subject Noncompliance with Study Medication or Study Visits | 1 (2.4%) | 0 (0.0%) | 1 (1.1%) |
| Other[w] | 2 (4.8%) | 1 (2.0%) | 3 (3.2%) |

[w]Other - In the Placebo group, one subject discontinued due to lack of efficacy and one subject discontinued due to pregnancy. In the OBS 2 mg bid group one subject discontinued due to uncontrolled diabetes.

Select clinical study subject demographics are provided in Table 7.

TABLE 7

Clinical Study Subject Demographics

| | Placebo | OBS 2 mg bid | All Subjects |
|---|---|---|---|
| Age (years)[1] | | | |
| n | 42 | 51 | 93 |
| Mean (SD) | 20.8 (7.50) | 22.3 (7.92) | 21.6 (7.73) |
| <18 Years of Age | 17 (40.5%) | 18 (35.3%) | 35 (37.6%) |
| >18 Years of Age | 25 (59.5%) | 33 (64.7%) | 58 (62.4%) |
| Sex | | | |
| Male | 29 (69.0%) | 35 (68.6%) | 64 (68.8%) |
| Ethnicity | | | |
| Hispanic or Latino | 1 (2.4%) | 0 (0.0%) | 1 (1.1%) |
| Race | | | |
| Black or African American | 0 (0.0%) | 3 (5.9%) | 3 (3.2%) |
| White | 40 (95.2%) | 48 (94.1%) | 88 (94.6%) |
| Multiple Race Checked | 2 (4.8%) | 0 (0.0%) | 2 (2.2%) |
| Months Since EoE Diagnosis[2] | | | |
| n | 40 | 47 | 87[3] |
| Mean (SD) | 35.98 (42.189) | 37.99 (33.823) | 37.07 (37.684) |
| Height (cm) | | | |
| n | 42 | 51 | 93 |
| Mean (SD) | 170.69 (13.023) | 173.62 (9.943) | 172.30 (11.465) |
| Weight (kg) | | | |
| n | 42 | 51 | 93 |
| Mean (SD) | 67.80 (17.262) | 72.01 (16.892) | 70.11 (17.097) |

[1]Age is calculated from the date of birth to the date of informed consent signed.
[2]Defined as the number of days between the date of the EoE diagnosis and the Screening Visit Date, calculated in months [i.e., (Screening date-EoE Diagnosis date + 1)/365.25/12))], and rounded to 1 decimal place.
[3]Of the 93 subjects randomized, 6 were diagnosed at Screening.

A paper-based 4-question DSQ (see FIG. 21) was converted into an electronic format for hand-held devices, as illustrated in the process flow in FIG. 20. In this case, the items are text-based questions and the DSQ is a 4-question instrument. Questions 2 and 3 (Q2 and Q3) were used to calculate a DSQ Score. Questions 1 and 4 (Q1 and Q4) are ancillary to the DSQ Score. The DSQ Score was calculated by applying the following algorithm to the values obtained from the DSQ:

$$DSQ\ Score = [(\text{Sum of points from } Q2 \text{ and } Q3 \text{ in the daily } DSQ) \times 14]/(\text{Number of diaries reported with non-missing data})$$

The DSQ Score for the primary endpoint was calculated as above by summing the points from Q2 and Q3 from each reported daily diary with non-missing data, and dividing this by the number of reported daily diaries with non-missing data in the selected 14-day period. This quotient was then multiplied by 14. The DSQ Score calculated during the 14-day period prior to Baseline Visit 2 is the Baseline DSQ Score. The DSQ Score calculated during the 14-day period prior to the Final Treatment Period Evaluation is the Final Treatment DSQ Score.

A DSQ+Pain Score was also calculated by applying the following algorithm to the values obtained from the DSQ.

$$DSQ\ Score + Pain = [(\text{Sum of points from } Q2, Q3 \text{ and } Q4 \text{ in the daily } DSQ) \times 14]/(\text{Number of diaries reported with non-missing data})$$

Baseline patient characteristics are shown in Table 8.

TABLE 8

Clinical Study Subject Disposition

|  | Placebo | OBS 2 mg bid | All Subjects |
|---|---|---|---|
| Baseline Peak Eosinophil Count (/HPF)[1] | | | |
| Proximal (n) | 36 | 48 | 84 |
| Mean (SD) | 53.3 (58.61) | 100.9 (99.60) | 80.5 (87.35) |
| Mild (n) | 42 | 48 | 90 |
| Mean (SD) | 94.4 (80.50) | 103.8 (67.53) | 99.4 (73.79) |
| Distal (n) | 42 | 51 | 93 |
| Mean (SD) | 95.8 (74.64) | 107.4 (79.53) | 102.2 (77.17) |
| Baseline Total Endoscopy Score[2] | | | |
| n | 42 | 51 | 93 |
| Mean (SD) | 7.0 (3.31) | 7.7 (3.54) | 7.4 (3.44) |
| Baseline DSQ Score[3] | | | |
| n | 41 | 51 | 92 |
| Mean (SD) | 28.97 (13.541) | 30.42 (15.903) | 29.77 (14.835) |
| Subjects on Concomitant Proton Pump Inhibitors | 29 (69.0%) | 34 (66.7%) | 63 (67.7%) |

[1]Peak eosinophil counts from central pathology.
[2]The total endoscopy score is the sum of the endoscopy scores for proximal and distal locations based on local site scoring.
[3]The DSQ score is calculated based on daily diaries during the 14 day window prior to Baseline Visit 2.

Figure 22:
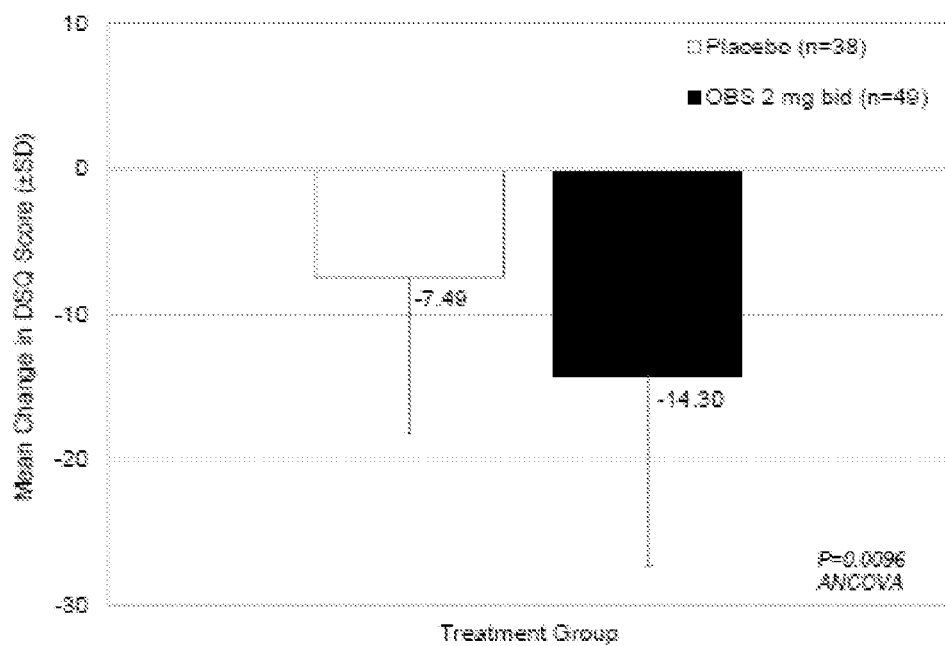
FIG. 22 depicts data from the clinical study of Example 2; specifically, the mean change in DSQ Score from Baseline to the Final Treatment Period Evaluation.
Figure 23:
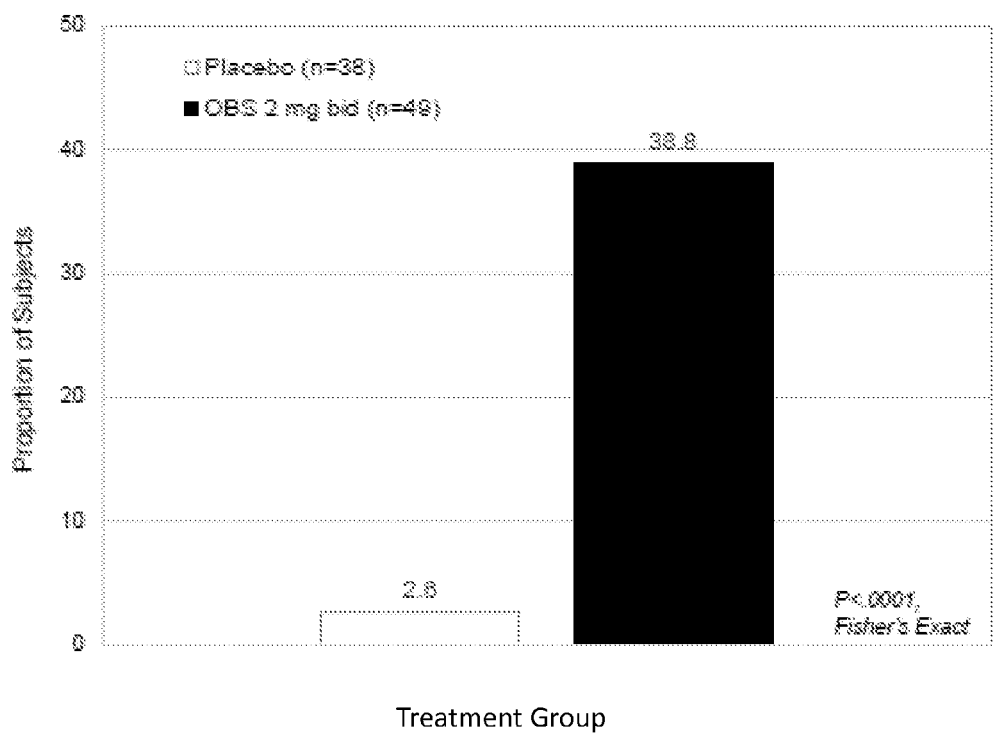
FIG. 23 depicts data from the clinical study of Example 2; specifically, the proportion of patients exhibiting a histologic response to treatment at the Final Treatment Period Evaluation.

The change in DSQ Score from Baseline to the Final Treatment Period Evaluation is shown in FIG. 22. The proportion of patients exhibiting a histologic response to treatment at the Final Treatment Period Evaluation is shown in FIG. 23.

Figure 24:
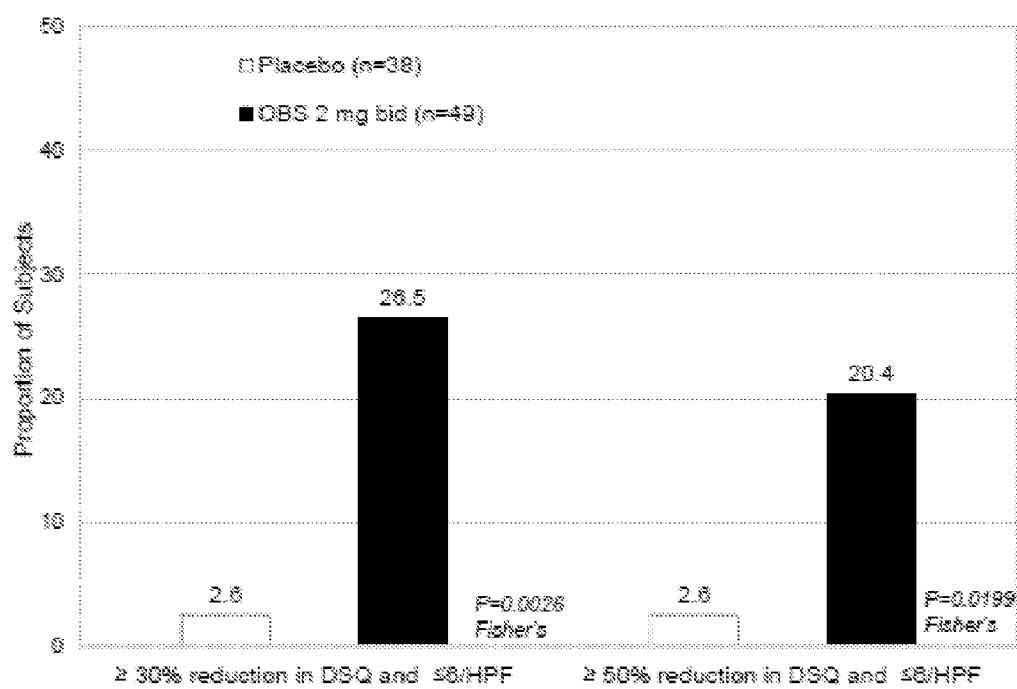
FIG. 24 depicts data from the clinical study of Example 2; specifically, the proportion of subjects who were responders and overall responders to OBS.

The proportion of subjects who were overall responders, which is defined as a reduction in the DSQ Score of >30% from Baseline to the Final Treatment Period Evaluation and a peak eosinophil count of <6/HPF across all available esophageal levels at the Final Treatment Period Evaluation (week 16), is shown in FIG. 24. The proportion of subjects who were responders, which is defined as a reduction in the DSQ Score of >50% from Baseline to the Final Treatment Period Evaluation and a peak eosinophil count of <6/HPF across all available esophageal levels at the Final Treatment Period Evaluation (week 16), is also shown in FIG. 24.

Figure 25:
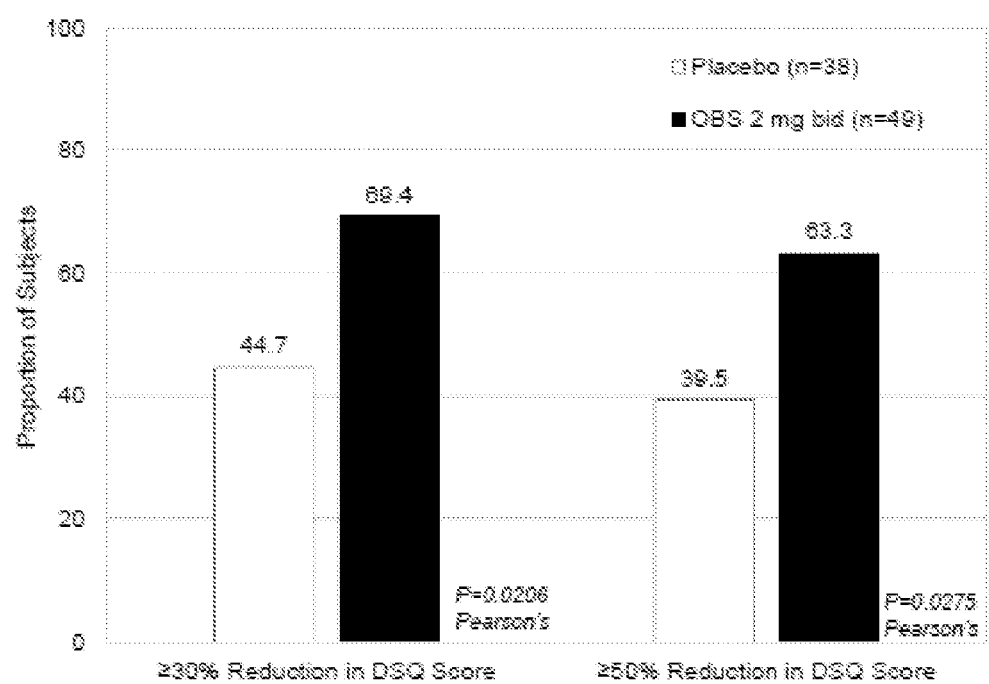
FIG. 25 depicts data from the clinical study of Example 2; specifically, the proportion of subjects with a symptom response as determined by a reduction in the DSQ Score of >30% or >50% from Baseline to the Final Treatment Period Evaluation.

The proportion of subjects with a symptom response as determined by a reduction in the DSQ Score of >30% or >50% from Baseline to the Final Treatment Period Evaluation is shown in FIG. 25.

Figure 26:
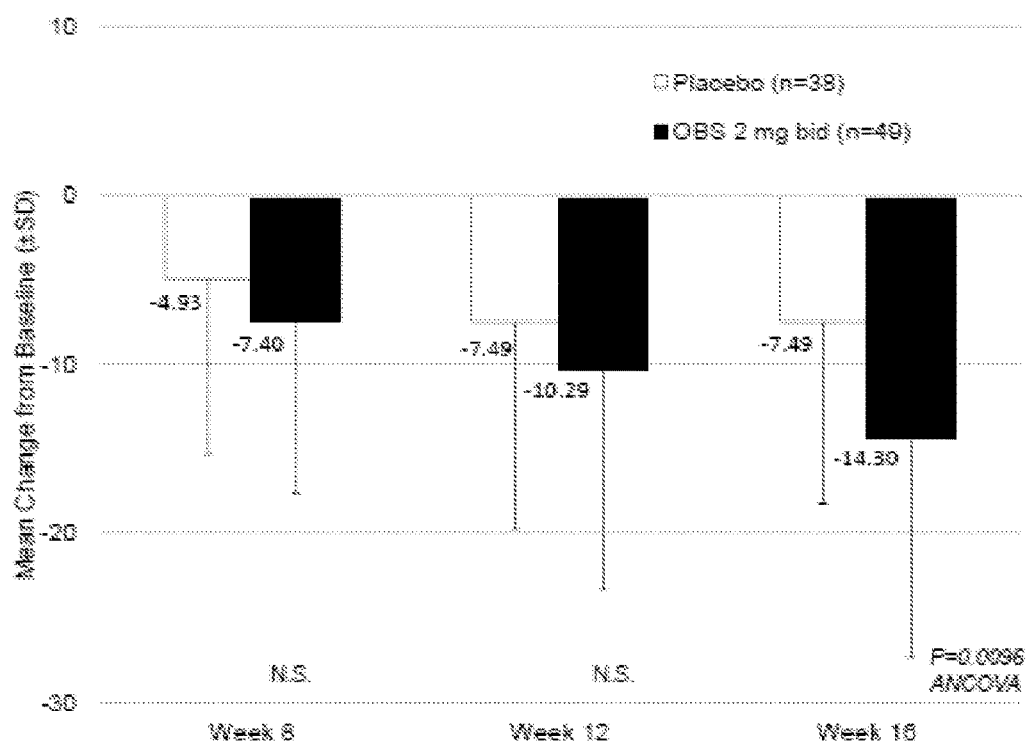
FIG. 26 depicts data from the clinical study of Example 2; specifically, the mean change from Baseline at each post-Baseline visit (weeks 8, 12 and 16) as determined by the DSQ Score.

The mean change from Baseline at each post-Baseline visit (weeks 8, 12 and 16) as determined by the DSQ Score is shown in FIG. 26.

A summary overview of the efficacy data is presented in Table 9.

TABLE 9

Overview of Efficacy Data at Week 16: MITT Analysis Set

| Efficacy Endpoints | Placebo (N = 38) | OBS 2 mg bid (N = 49) | p-value | Data Table |
|---|---|---|---|---|
| Co-primary endpoint-Pathologist reported | n = 38 | n = 49 | | |
| Histologic responders-Peak eosinophils <6/HPF [n | 1 (2.6) | 19 (38.8) | <0001[a] | 14.2.2.1 |
| Co-primary endpoint-Subject reported | n = 38 | n = 49 | | |
| Dysphagia Symptom Questionnaire (DSQ) score | | | | |
| Mean baseline | 28.99 | 29.27 | | |
| LS mean change from baseline | −7.53 | −14.27 | | |
| LS mean difference from placebo (95% CI) | | −6.75 (−11.8, −1.7) | 0.0096[b] | 14.2.1.1 |
| Symptom responders - % reduction in DSQ score | n = 38 | n = 49 | | |
| >30% reduction in DSQ score [n (%)] | 17 (44.7) | 34 (69.4) | 0.0206` | 14.2.6.1 |
| >50% reduction in DSQ score [n (%)] | 15 (39.5) | 31 (63.3) | 0.0275` | 14.2.6.1 |
| Histopathology epithelial features (stage + grade) (Pathologist reported) | n = 37 | n = 49 | | |
| Mean baseline | 46.1 | 54.5 | | |
| LS mean change from baseline | −1.26 | −23.87 | | |
| LS mean difference from placebo (95% CI) | | −22.61 (−30.7, −14.6) | <0001[b] | 14.2.12.1 |
| Endoscopy score-proximal and distal (max = 20) (Physician reported) | n = 38 | n = 49 | | |
| Mean baseline | 6.9 | 7.7 | | |
| LS mean change from baseline | 0.19 | −3.58 | | |
| LS mean difference from placebo (95% CI) | | −3.76 (−5.2, −2.4) | <0001[b] | 14.2.13.1 |
| Physician Global Assessment (0-100 mm) | n = 38 | n = 49 | | |
| Mean baseline | 55.2 | 59.5 | | |
| LS mean change from baseline | −10.16 | −28.61 | | |
| LS mean difference from placebo (95% CI) | | −18.44 (−29.6, −7.3) | 0.0015[b] | 14.2.15.1 |
| Patient Global Impression of Change (dysphagia) | n = 38 | n = 49 | | |
| Distribution across the 7 rating categories | | | 0.1170[d] | 14.2.17.1 |
| Responders-Histologic + symptom (dysphagia) | n = 38 | n = 49 | | |
| Peak eos <6/HPF+ >30% reduction in DSQ score [n | 1 (2.6) | 13 (26.5) | 0.0026[a] | 14.2.3.1 |
| Peak eos <6/HPF+ >50% reduction in DSQ score [n | 1 (2.6) | 10 (20.4) | 0.0199[a] | 14.2.5.1 |
| Symptom responders - % reduction in DSQ+pain | n = 38 | n = 49 | | |
| ≥30% DSQ+pain symptom response [n (%)] | 18 (47.4) | 33 (67.3) | 0.0606[c] | 14.2.7.1 |
| ≥50% DSQ+pain symptom response [n (%)] | 15 (39.5) | 32 (65.3) | 0.0165` | 14.2.7.1 |
| Pain score-DSQ question 4 - Subject reported | n = 38 | n = 47 | | |
| Mean baseline | 8.45 | 9.90 | | |

TABLE 9-continued

Overview of Efficacy Data at Week 16: MITT Analysis Set

| Efficacy Endpoints | Placebo (N = 38) | OBS 2 mg bid (N = 49) | p-value | Data Table |
|---|---|---|---|---|
| LS mean change from baseline | −3.08 | −4.87 | | |
| LS mean difference from placebo (95% CI) | | −1.80 (−4.0, 0.4) | 0.1091[b] | 14.2.10.1 |

Abbreviations:
CI = confidence interval;
DSQ = Dysphagia symptoms questionnaire;
eos = eosinophils;
HPF = high powered field;
LS = least squares;
max = maximum;
MITT = modified intent-to-treat.
[b] p-value was determined using 2-tailed Fisher's exact test. p-value was determined using an ANCOVA model including treatment group as a factor and baseline score as a covariate.
[c] p-value was determined using Pearson's chi-square test.
[d] p-value for comparison of the treatment difference across the 7 global rating categories was determined by Cochran-Mantel-Haenszel row mean score test.

Discussion and Conclusions

As can be seen from the data presented in FIGS. 22-28 and Table 9, the co-primary endpoints indicated treatment efficacy with the oral budesonide solution. Furthermore, the data also demonstrate a statistically significant correlation between the change in DSQ Score from Baseline to Final Treatment Period Evaluation and the changes observed in histologic features during the same period. Thus, Example 2 demonstrates that an electronic DSQ as disclosed herein is an accurate measure of the efficacy of EoE treatment regimens.

While certain embodiments have been shown and described herein, it will be apparent to those skilled in the art that such embodiments are provided by way of example only. Numerous variations, changes, and substitutions will now occur to those skilled in the art and are considered to be within the scope of the disclosure herein. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating dysphagia, the method comprising:
   a. providing, via a digital processing device, a daily patient questionnaire to a patient as a diagnostic tool, said questionnaire comprising:
      i. at least one of an avoidance question determining whether the patient avoided solid food;
      ii. at least one of a frequency question determining frequency of the patient's symptom;
      iii. at least one of a response question determining what action, if any, the patient took to correct or relieve the symptom;
      iv. at least one of a pain question determining the amount of pain the patient experienced during the symptom;
      wherein the questionnaire presents at least a three question combination of the avoidance question, the frequency question, the response question, and the pain question;
   b. applying, via the digital processing device, an algorithm to answers to said combination of questions to determine a daily average score,
      wherein the algorithm:
      scores the at least one avoidance question from 0 to 1;
      scores the at least one frequency question from 0 to 1;
      scores the at least one response question from 0 to 5;
      sums the scores of all the questions presented in the questionnaire; and
      calculates the daily average score based on a plurality of scored questionnaires;
   c. evaluating the daily average score against a threshold, and
   d. administering a corticosteroid therapy to the patient when the daily average score exceeds the threshold.

2. The method of claim 1, further comprising communicating patient answers to a centralized database via a software module.

3. The method of claim 1, wherein the threshold is an average score per questionnaire between 1 and 2.

* * * * *